US012599763B2

(12) United States Patent
Tehrani et al.

(10) Patent No.: US 12,599,763 B2
(45) Date of Patent: Apr. 14, 2026

(54) ENDOVASCULAR LEAD DESIGN AND DELIVERY SYSTEMS

(71) Applicant: RMX, LLC, San Francisco, CA (US)

(72) Inventors: Amir J. Tehrani, San Francisco, CA (US); Albert Burdulis, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 366 days.

(21) Appl. No.: 18/175,424

(22) Filed: Feb. 27, 2023

(65) Prior Publication Data

US 2023/0270998 A1 Aug. 31, 2023

Related U.S. Application Data

(60) Provisional application No. 63/268,616, filed on Feb. 28, 2022.

(51) Int. Cl.
*A61N 1/05* (2006.01)

(52) U.S. Cl.
CPC ......... *A61N 1/0565* (2013.01); *A61N 1/0551* (2013.01)

(58) Field of Classification Search
CPC .. A61N 1/0565; A61N 1/0551; A61N 1/3611; A61N 1/36114; A61N 1/0558; A61N 1/3601; A61N 1/36117; A61B 18/1492; A61B 2018/00404; A61B 2018/00511; A61B 5/0215; A61B 5/026; A61B 2018/0022; A61B 5/02007; A61B 5/4041; A61B 5/6853; A61B 2018/00434
See application file for complete search history.

(56) References Cited

U.S. PATENT DOCUMENTS

| | | | |
|---|---|---|---|
| 8,412,350 B2 * | 4/2013 | Bly | A61N 1/0558 |
| | | | 607/116 |
| 10,952,665 B2 * | 3/2021 | Goedeke | A61M 25/10 |
| 2022/0287768 A1 * | 9/2022 | Franceschi | A61N 1/056 |

* cited by examiner

*Primary Examiner* — Mark W. Bockelman
(74) *Attorney, Agent, or Firm* — Levine Bagade Han LLP

(57) ABSTRACT

Endovascular lead design and delivery systems are described herein. One variation of an endovascular lead apparatus may generally comprise an elongate body having a proximal portion and a distal portion, one or more electrodes positioned along a first side of the distal portion, a tray positioned along a second side of the distal portion opposite to the first side, and one or more frame members positioned along the tray and which are reconfigurable from a low-profile delivery configuration to an expanded deployed configuration, wherein expansion of the one or more frame members to the expanded deployed configuration reconfigures the distal portion into contact against a tissue wall for energy delivery via the one or more electrodes.

9 Claims, 14 Drawing Sheets

EMG Diaphragm (Intrinsic Activity)

Flow

TV

Stimulation Marker

FIG. 4A

Flow

FIG. 4B

Tidal
Volume

FIG. 4C

Simulation
Marker

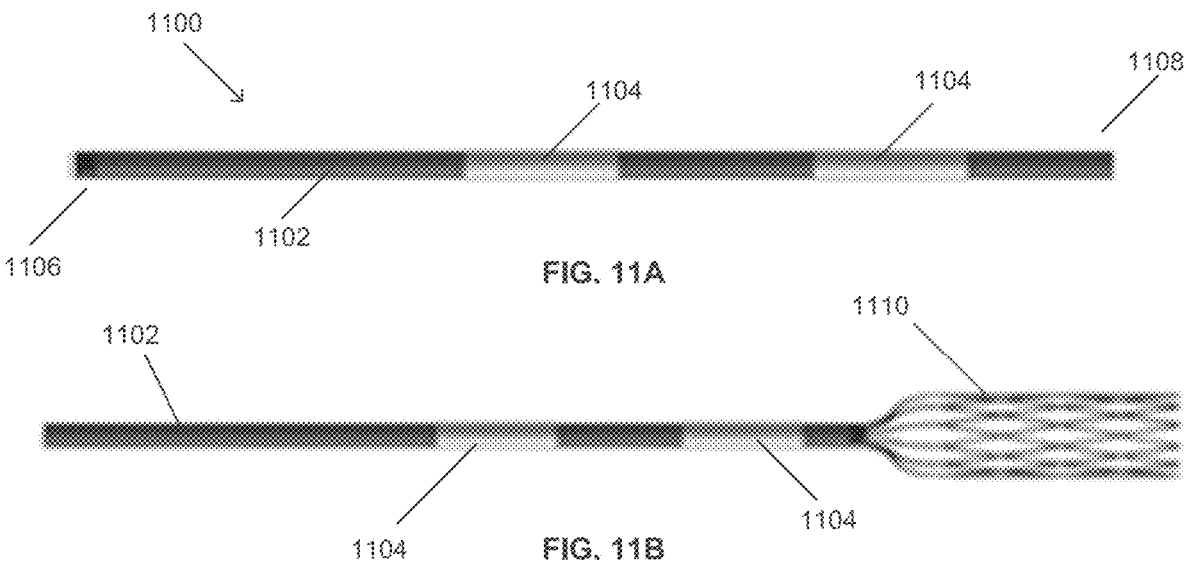
FIG. 11A
FIG. 11B
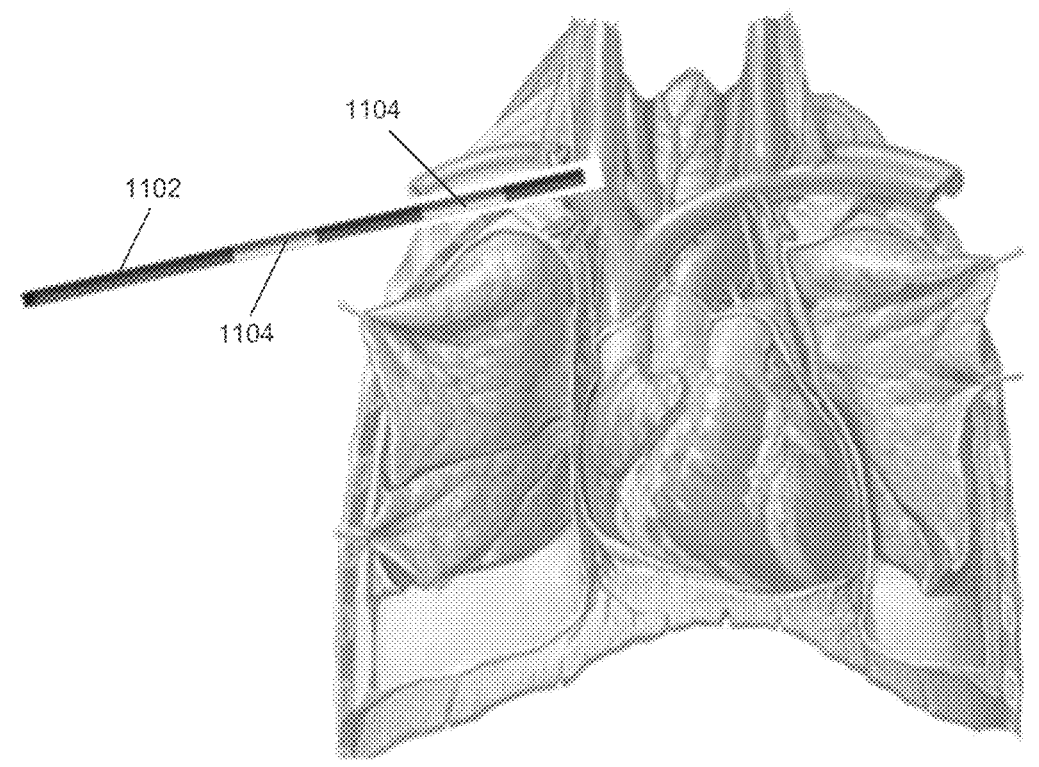
FIG. 12

ENDOVASCULAR LEAD DESIGN AND DELIVERY SYSTEMS

CROSS-REFERENCE TO RELATED APPLICATIONS

This application claims the benefit of priority to U.S. Provisional Application No. 63/268,616 filed Feb. 28, 2022, the contents of which are incorporated herein by reference in their entirety.

FIELD OF THE INVENTION

The present invention relates to devices and methods for treating a variety of conditions, disorders or diseases using a sheath system with deployable mapping electrodes. The present invention also relates to treating heart failure (or dysfunction) and other cardiovascular disorders, in particular, using one or more implantable or non-implantable sensors along with phrenic nerve stimulation to reduce intrathoracic pressure and thereby reduce pulmonary artery, atrial, renal, and ventricular pressures leading to reduced complications and hospitalization. The present invention targets treating acute decompensated heart failure (ADHF) utilizing a temporary or removable catheter or electrode as well as a fully chronic implantable device for long-term treatment of heart failure, sleep apnea, critical care and mechanical ventilation, and pulmonary hypertension patients.

BACKGROUND OF THE INVENTION

Neurostimulation systems typically include one or more electrode carrying neurostimulation leads, which are positioned temporarily or implanted at a desired stimulation site. A neurostimulation device such as an implantable pulse generator can be implanted remotely from the stimulation site and coupled to the neurostimulation leads in order to deliver electrical pulses through the neurostimulation leads to stimulate the tissue.

Heart failure is a complex disease with many forms and causes. In general heart failure is defined as a condition where the cardiac output is not adequate to meet the metabolic needs of the body, either at rest or with exercise. Heart failure may be preceded by heart dysfunction, including, but not limited to ventricular dysfunction.

There are two forms of heart failure, one where the hearts ability to expel the blood is impaired (systolic heart failure), another where there is a defect in ventricular filling (diastolic heart failure). Each can occur in isolation or together.

Current treatments for heart failure are available to slow the progress of the disease but do not cure the disease. Despite all the current therapeutic options, studies show that more than half of heart failure patients die within 5 years of their diagnosis.

Accordingly it would be desirable to provide new and useful treatments for heart failure or other cardiac/cardiovascular disease.

Pacemakers have been useful where there are cardiac bradyarrhythmias. Defibrillators are primarily used to prevent sudden cardiac death and therefore have not improved the status of heart failure patients nor have they improved quality of life. Cardiac Resynchronization Therapy devices (CRTs) have been useful or in patients with significant interventricular delay or in preventing cardiac tachyarrhythmias or sudden cardiac death (CRT-Ds). There are many heart failure patients who may not substantially benefit from one or more of these treatments or may not have an improved quality of life from such treatments. For example, CRTs have not been approved for patients with ejections fractions greater than 35% and thus are not available for diastolic heart failure patients who typically have ejection fractions greater than 50%, or for systolic patients with an ejection fraction greater than 35%. Some studies show diastolic heart failure to account for up to ⅓ of the patients presenting with heart failure. In addition, because the current treatments do not cure heart failure, additional treatment that may be used in combination with existing treatment may be beneficial to the patients. Other devices such as temporary or chronic implants stimulate the vagal nerve or cardiac plexus nerves to reduce the heart rate and/or improve cardiac contractility and achieve improved cardiac output.

Many of the drugs such as calcium channel blockers, beta blockers, ACE inhibitors, diuretics, nitrates have had varying degrees of effect on different manifestations of heart failure. However, not all are useful to treat all heart failure patients. Furthermore, due to side effects some patients withdraw from treatment. Pharmacological therapeutic approaches to diastolic heart failure currently recommend diuretics and nitrates while the efficacy is uncertain for all diastolic heart failure patients with calcium channel blockers, beta blockers, ACE inhibitors. Inotropic agents are not recommended for diastolic patients. Accordingly it would be desirable to provide treatment for heart failure that may be used alone or in combination with other heart failure treatments. It would also be desirable to provide alternative or supplementary treatment for diastolic heart failure patients.

Another cardiovascular condition that may exist with or without heart failure is hypertension. Hypertension is believed to worsen heart failure. It is also believed that hypertension may lead to diastolic heart failure. Studies have shown that treatment of hypertension reduces the incidence of heart failure by 30% to 50%. Accordingly it would be desirable to provide a treatment for hypertension.

In addition, a large percentage of heart failure patients also suffer from one or more forms of sleep apnea: obstructive sleep apnea or central sleep apnea, (each of which have significant clinical differences), or mixed apneas. These conditions are believed to worsen progression of heart failure. Obstructive sleep apnea is also believed to contribute to the development of heart failure, particularly through hypertension.

Oxygen desaturations at night, changes in intrathoracic pressure, and arousals may adversely affect cardiac function and eventually result in an imbalance between myocardial oxygen delivery and consumption. In heart failure patients with sleep apnea, there is believed to be an increased incidence of atrial fibrillation, ventricular arrhythmias and low left ventricular ejection fraction. Atrial fibrillation may be caused in part by increased right heart afterload due to hypoxic vasoconstriction which produces pulmonary hypertension. Periodic breathing such as Cheyne-Stokes associated with CSA, create wide fluctuations in intrathoracic pressure with a negative cardiovascular impact. Central sleep apnea sometimes goes undiagnosed in heart failure patients. The untreated central sleep apnea may trigger a negative chain of events that leads to worsening of heart failure.

Obstructive sleep apnea is believed to elicit a series of mechanical, hemodynamic, chemical, neural and inflammatory responses with adverse consequences for the cardiovascular system for example, as described in *Sleep Apnea and Heart Failure Part I: Obstructive Sleep Apnea*. Bradley, Douglas T, MD, Floras, John S., MD D Phil, *Circulation*

Apr. 1, 2003. Many of these effects are believed to exacerbate conditions of heart failure. Among these responses, increases in blood pressure as well as increases in sympathetic activity are associated with obstructive apneas. Obstructive sleep apnea also causes significant changes in intrathoracic pressure during apneic episodes applying further pressure on the heart.

Accordingly it would be desirable to treat sleep apnea in heart failure to reduce the negative effects of the apnea on the patient's disease status.

CPAP is the most common treatment for obstructive sleep apnea and has been proposed for central sleep apnea. CPAP requires an external device and patient compliance. In addition, its cardiovascular effects are currently unclear and some researchers believe that it can exacerbate heart failure in some patients, particularly where positive forced pressure has a negative effect on a heart failure patient, such as, for example, in patients where a reduced ventricular filling would significantly reduce cardiac output. Diaphragm stimulation has been proposed to treat central sleep apnea by stimulating when apnea has occurred. However, the stimulation is provided after the apnea event has occurred rather than preventing the apnea event. Hypoglossal nerve stimulation has been proposed to treat obstructive sleep apnea by increasing patency in the upper airway to allow respiration.

It would accordingly be desirable to provide a treatment for sleep apnea that has a symbiotic therapeutic effect in treating heart failure or other cardiac/cardiovascular disease.

It would further be desirable to provide a treatment for heart failure patients with sleep apnea that provides a separate or additional function of treating heart failure.

Research has shown that voluntary control of breathing can improve cardiac disease, including hypertension and heart failure. It is believed that the reason for this is a biofeedback that exists between the cardiac and respiratory systems due to baroreceptor based reflexes, and also a common central nervous control. Biofeedback systems for breathing control have been provided. However, they require patient compliance and diligence. Furthermore, because they require patient compliance, the therapy can only occur during waking hours.

Heart failure is a chronic condition which leads to a reduction in cardiac output and an increase in pulmonary pressures which in turn leads to pulmonary congestion and hospitalization. Yet various studies have shown significant increases in stroke volume and cardiac output, particularly in patients who have undergone a CABG procedure, when negative extrathoracic pressure is reduced. For example, results may be seen in further detail in the following:

Parker, J. et al, "Reducing Cardiac Filling Pressure Lowers Norepinephrine Spillover in Patients With Chronic Hear Failure", Circulation, 2000; 101:2053-2059.

CHATURVEDI, R. et al., "Use of Negative Extrathoracic Pressure to Improve Hemodynamics After Cardiac Surgery", The Annals of Thoracic Surgery, 2008; 85, pp. 1355-1360, 2008.

GOTTLIEB, J. et al., "Hypoxia, Not the Frequency of Sleep Apnea, Induces Acute Hemodynamic Stress in Patients With Chronic Heart Failure", Journal of the American College of Cardiology, Vol. 54, No. 18, pp. 1706-1712, Oct. 27, 2009.

MERCHANT, F. et al., "Implantable Sensors for Heart Failure", Circulation: Arrhythmia and Electrophysiology, 2010; 3, pp. 657-667, 2010.

BOCCHIARDO, M. et al., "Intracardiac impedance monitors stroke volume in resynchronization therapy patients", Europace: Journal of the European Heart Rhythm Association, (2010) 12, pp. 702-707, Feb. 25, 2010.

KASZALA, K. et al., "Device Sensing: Sensors and Algorithms for Pacemakers and Implantable Cardioverter Defibrillators", Circulation, Journal of the American Heart Association, 2010; 122, pp. 1328-1340, Sep. 28, 2010.

LAU, C. et al., "Optimizing heart failure therapy with implantable sensors", Journal of Arrhythmia, 28(2012), pp. 4-18, Mar. 9, 2012.

Each of these references is incorporated herein by reference in its entirety and for any purpose.

Previous attempts have been made to utilize an implantable medical device to stimulate a patient's diaphragm to affect cardiac output. For instance, U.S. Pat. No. 7,277,757 to Casavant et al. discloses an implantable medical device that stimulates a nerve, such as a phrenic nerve, associated with respiration to cause a diaphragm of a patient to contract. The implantable medical device receives a signal (e.g., detecting a ventricular tachyarrhythmia, sensing a pressure that indicates a need for increased cardiac output, or receiving a signal from a patient via a patient activator) that indicates a need for increased cardiac output and stimulates the nerve in response to the signal. Stimulation of the nerve may increase cardiac output of a beating or defibrillating heart.

However, Casavant et al. fails to disclosure pressure sensing and creating lung volume with a reduction in intrathoracic pressure. Moreover, Casavant synchronizes its stimulation to the pacing of the heart and increases the amplitude of at least some of the pacing pulses rather than providing for a sustainable stimulation over a continuous period of time.

SUMMARY OF THE INVENTION

A neurostimulation lead system may be comprised of a commercial lead mounted and connected to a flexible frame fabricated from nitinol or other biocompatible material where the frame may be inserted and advanced via flexible catheter body through a vessel into proximity of a nerve to be stimulated. The frame can be constructed of nitinol wires where the nitinol wires act as a "guidewire" which can be inserted through a lumen. Alternatively, the lead can be placed and fastened to the frame such that as the frame expands, the lead may adhere to the vessel wall in the intended position where the lead is facing the targeted nerve through the vessel. The frame and lead system may be housed or inserted inside a sheath or mapping sheath. Specific markers and labels on the sheath and sheath catheter may provide orientation of the lead and electrodes in reference to the targeted nerve. As the sheath is pulled away (e.g., pulled proximally), the nitinol frame may slowly expand in the intended location within the vessel and orientation relative to the nerve to be stimulated. The frame/lead system can also be collapsed by pushing the sheath distally over the frame and repositioned and released again and/or removed from the vessel.

One variation of an endovascular lead apparatus may generally comprise an elongate body having a proximal portion and a distal portion, one or more electrodes positioned along a first side of the distal portion, a tray positioned along a second side of the distal portion opposite to the first side, and one or more frame members positioned along the tray and which are reconfigurable from a low-profile delivery configuration to an expanded deployed configuration, wherein expansion of the one or more frame members to the expanded deployed configuration reconfigures the distal portion into contact against a tissue wall for energy delivery via the one or more electrodes.

One variation of a method of stimulating a nerve may generally comprise advancing an elongate body within a vessel and into proximity of a nerve body to be stimulated, confirming a location of the nerve body via one or more mapping electrodes positioned along the elongate body, exposing a distal end of the elongate body such that one or more frame members positioned along the distal end reconfigure to urge a first side of the distal portion into contact against an inner surface of the vessel, and actuating one or more treatment electrodes positioned along the first side to deliver a treatment stimulation through the inner surface and into the nerve body.

In accordance with the invention, stimulation is provided to the diaphragm or phrenic nerve to elicit a diaphragm response to thereby provide a therapeutic effect for a heart failure or other cardiac or cardiovascular patient.

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients. Normalizing herein may include for example, bringing a physiological parameter into a normal or healthy region for patients or for a particular patient, or to a level appropriate for a condition or state of a patient.

In accordance with another aspect of the invention stimulation is provided to control breathing to reduce respiration rate and thereby reduce hypertension, reduce sympathetic nerve bias, and/or provide improved blood gas levels.

In accordance with another aspect of the invention stimulation is provided to control minute ventilation to therapeutically effect blood gas levels.

In accordance with another aspect of the invention, stimulation is provided to create a deep inspiration or an increased tidal volume to thereby reduce sympathetic nerve bias, improve blood gas levels, stimulate reflexes for example the Hering-Bruer reflex related to activating stretch receptors, increase lung volume, normalize or reset breathing or provide other beneficial therapies to improve cardiovascular function or heart failure condition.

In accordance with another aspect of the invention stimulation may be provided to modulate intrathoracic pressure to thereby produce a therapeutic effect. Modulation of intrathoracic pressure is expected to impact sympathetic activation and improve heart conditions. It is known that in chronic heart failure settings, increased cardiac filling pressures and/or pulmonary pressures may cause a direct or indirect reflex increase in sympathetic efferent outflow to the heart. Therefore, a sustained reduction or average reduction in intrathoracic pressure through modulation of intrathoracic pressure could have an opposite effect and reduce sympathetic efferent outflow to the heart. One would expect to reduce norepinephrine spillover through intrathoracic pressure modulation which is beneficial to the heart failure patient. Parker et al. used a lower body pressure chamber to show certain reduction in body pressure leads to reduction in cardiac filling pressures leading to reduction in norepinephrine spillover in acute setting. Longer term application this therapy has potential to improve the heart failure and also remodel the cardiac tissue.

The devices and methods described may achieve similar results through various modes of phrenic nerve and/or diaphragm stimulation. These stimulation modalities include low-level stimulation overlapped with patient intrinsic breathing, diaphragm bias, breath augmentation, increase in tidal volume, increase in inspiration duration, deep inspiration, breathing entrainment, manipulation of exhalation period and volume, increasing and maintain resting lung volume or functional residual capacity, sustained stimulation during inspiration and/or exhalation, continuous stimulation, stimulation synchronized with respiratory cycles, or cardiac cycles, and/or duty-cycled type stimulation based on a percentage of time, for example, 20% of the time during the day or night and when patient is sleep or awake. The duty-cycled type stimulation could be synchronized to a respiratory cycle or not.

In accordance with another aspect of the invention, stimulation may be provided to modulate intrathoracic pressure targeting a sustained reduction in average central venous pressure to effectively reduce right arterial and right ventricular pressures and pulmonary wedge pressure. Reduction in right ventricular pressure in heart failure patients leads to increase stroke volume and therefore cardiac output. The sustained increase in cardiac output though reduction in filling pressure will lead to reductions in pulmonary congestion which is a major reason for acute heart failure decompensation and therefore hospitalization. Some other hemodynamic effects of this stimulation could be reduction in heart rate as results of increased in cardiac output and/or reduction in filling pressures.

In accordance with another aspect of the invention, stimulation may be provided to modulate intrathoracic pressure targeting a sustained or incremental reduction in renal pressure or the average renal pressure to improve kidney function and filtration. Abnormal renal function is common in acute and chronic heart failure. It is expected a change in blood volume, cardiac filling pressures, central venous pressure, atrial or ventricular pressures, cardiac output, and/or hemodynamics intervention could lead to improvement of renal function. Intrathoracic pressure modulation could have an impact on pressure within inferior and superior vena cava as well as central venous pressures. Activation of renal sympathetic activity through modulation and manipulation of these pressures could have an impact on kidney pressure and blood transfer rate and ultimately kidney glomerular filtration rate (GFR) and leading to reduction in kidney failure as well as reducing congestion or blood backing up into the lungs through increased filtration. Any of the mentioned phrenic nerve or diaphragm stimulation modalities included in this application could be applied at various situations depending on the need of the patient and sensed parameters. Literature has shown that elevated cardiac filling pressures are associated with reduced GFR. Therefore the present invention tries to reduce cardiac filling pressure through phrenic nerve stimulation and to increase GFR.

In accordance with another aspect of the invention, intrathoracic pressure modulation could be used to treat patients with pulmonary hypertension. Pulmonary hypertension is result of increased pulmonary pressures. Reduction or modulation of intrathoracic pressure could lead to reduction or treatment of pulmonary hypertension.

In accordance with another aspect of the invention the stimulation could be activated by the patient using an external device. The stimulation could be also activated by sensing increased physical activity through an activity sensor or increased in heart rate or respiration rate or other mechanism indicating need for supplemental cardiac output or reduction in filling pressures. For example, a thoracic or lungs impedance sensor or a list of sensors including in the referenced publication cold be used to activate stimulation to deliver therapy to improve hemodynamics.

In accordance with another aspect of the invention stimulation is provided to reduce breathing disorders to thereby improve condition of a heart failure patient.

In accordance with another aspect of the invention a combined cardiac rhythm management device including leadless devices and diaphragm/phrenic nerve stimulation device is provided to provide an enhanced combined treatment device.

In accordance with another aspect of the invention, leadless phrenic nerve electrodes could be injected, delivered, or placed in the vicinity of the phrenic nerve and stimulation cold be performed through an external or integral pulse generator. The sensor or sensors to synchronize the stimulation could be also internal or external to the body.

In accordance with another aspect of the invention a combined vagal nerve, hypoglossal nerve, or cardiac plexus stimulation management device and diaphragm/phrenic nerve stimulation device is provided to provide an enhanced combined treatment device.

The system may also be utilized to provide a continuous or synchronized low level stimulation to the phrenic nerve or diaphragm overlapped with the patient's own intrinsic breathing to reduce an intrathoracic pressure and improve cardiac output. The patient's SaO2 levels may also be improved and the heart and respiration rates may be reduced.

Various mapping and/or neurostimulating electrodes may be utilized with the methods and devices described herein. For instance, such mapping and/or neurostimulating electrodes may be employed in conjunction with a cardiac pacemaking or defibrillation lead and more particularly a mapping and neurostimulation electrodes employed over the cardiac pacemaking or defibrillation lead while the cardiac lead is either in vivo and resident within the vascular structure. These electrodes may be placed simultaneously with neurostimulation electrodes or leads. The mapping and neurostimulation electrodes used in conjunction with the cardiac pacemaking or defibrillation lead herein is referred to as the mapping and neurostimulation electrodes.

The mapping and neurostimulation electrodes may be employed in conjunction with a cardiac lead and for interventional therapy such as neurostimulation to patients who have already had a cardiac lead installed.

Such electrodes also overcome many of the problems that exist with conventional cardiac leads or cardiac leads with integral neurostimulation electrodes. If a patient has been implanted with an existing, conventional cardiac lead and that same patient requires additional interventional neurostimulation at any point after the existing cardiac lead has been implanted, the original cardiac lead must be explanted and the entire cardiac lead must be replaced. The electrodes described herein may be installed over the excising cardiac lead and advanced down the cardiac lead body into a therapeutic position without removing or re-positioning the existing cardiac lead.

In addition, a conventional cardiac lead with integral neurostimulation electrodes, whether the neurostimulation electrodes are integral to the cardiac lead or whether the neurostimulation electrodes are sutured onto the cardiac lead, typically must be installed concurrently when the cardiac lead is originally installed into the patient. The relationship between the neurostimulation electrode and the cardiac electrode is fixed prior to implant and therefore positioning for either the neurostimulation electrodes or the cardiac electrode is sub-optimal.

Yet the electrodes described herein are completely independent and mobile and have the ability to be installed over an existing cardiac lead. Moreover, the mapping and neurostimulation electrodes can be positioned independently of the cardiac electrodes. This independent positioning ability allows for both mapping and neuro-stimulating electrodes as well as the cardiac electrode's positioning to be optimized.

The temporary or chronic mapping and neurostimulation electrodes could be inserted through several approaches including femoral, radial, right or left Subclavien veins or right or left jugular veins or in other transvenous approaches placed in veins or arteries overlapping right or left phrenic nerve. Some electrode systems/catheters could map and stimulate both phrenic nerves through transvenous approaches. In cases where there are needs for both phrenic nerves to be stimulated simultaneously, with delays, or in sequence, a single electrode/leads system or two electrode/leads systems could be deployed.

Lastly, a conventional cardiac lead with integral neurostimulation electrodes or neurostimulation electrodes sutured onto the cardiac lead body are iso-diametric and are aligned randomly. The random alignment could limit therapy because the electrical field if not focused towards the neural anatomy as the electrodes will not energize the nerve. The electrodes described herein are designed to deploy the neurostimulation electrodes and bias the neurostimulation electrode towards the vessel wall and in a position that is tangent to the neural anatomy residing outside the vessel wall. The biased or focused neurostimulation electrodes assure the electrical field induced by the neurostimulation electrodes is optimized towards the neural anatomy.

These and other aspects of the invention are set forth herein in the abstract, specification and claims.

BRIEF DESCRIPTION OF THE DRAWINGS

FIGS. 4A, 4B, and 4C illustrate respectively, flow, tidal volume and stimulation envelope signals corresponding to use of a device and method in accordance with an aspect of the invention.

FIG. 11A shows a sheath system with mapping electrodes.

FIG. 11B shows a deployed neurostimulation lead system.

FIG. 12 shows a mapping sheath and lead system with mapping electrodes inserted inside the right subclavian vein under imaging guidance.

DETAILED DESCRIPTION OF THE INVENTION

In accordance with one aspect of the invention, stimulation to elicit a diaphragm response is provided to increase or normalize lung volume and in particular to increase functional residual capacity. It is believed that stimulation to increase or to normalize lung volume or functional residual capacity may have one or more effects that may be therapeutic to cardiovascular or heart failure patients.

In accordance with this aspect of the invention stimulation may be provided using a device or method as described in one or more of the related patent applications set forth herein, to increase or normalize lung volume or functional residual capacity. For example, a bias stimulation may be provided to increase functional residual capacity or to bias lung volume for a period of time. It is believed that increasing functional residual capacity may have one or more therapeutic effects for heart failure or other cardiovascular patients, such as, for example, reducing effort required to breathe; improving gas exchange, improving SaO2 levels; providing a buffer to reduce fluctuations in blood gas levels and to reduce the likelihood of crossing the PCO2 apneic threshold; and reducing episodes of obstructive apnea in OSA patients and central sleep apnea episodes. Such buffer may also stabilize blood gases to counter fluctuations in gas levels caused by circulatory delay that may lead to Cheyne-Stokes respiration and Central Sleep Apnea. Other stimulation may be provided to achieve improved SaO2 levels or gas levels, for example, as set forth in the related patent applications which are incorporated completely and without limitation herein by reference. Other stimulation may be provided that may have the effect of normalizing lung volume, including but not limited to low frequency stimulation, low energy stimulation, or deep inspiration stimulation. These various stimulation techniques may also be provided or configured to have the effect of increasing SaO2 levels to reduce load on the heart and cardiac filling pressures.

Figure 1A:
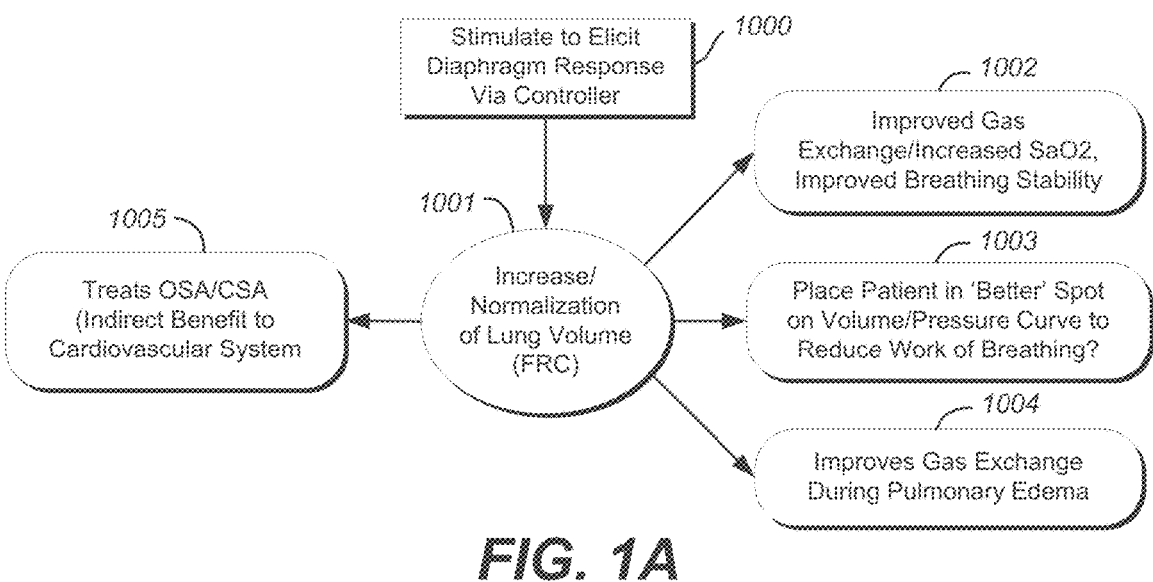
FIG. 1A is a chart illustrating examples of possible beneficial effects of stimulation in accordance with an aspect of the invention.

FIG. 1A illustrates stimulation provided with a device or method in accordance with the invention. Stimulation is provided using a device or method for stimulating tissue to elicit a diaphragm response 1000. Stimulation increases or normalizes lung volume or FRC 1001. The increase or normalization or lung volume may improve gas exchange; increase SaO2, and/or improve breathing stability 1002. The increase or normalization of lung volume or FRC may move a patient to a more optimal location on the volume pressure curve 1003 as described in more detail with respect to FIG. 1B. Providing stimulation to increase FRC may also allow improved gas exchange during pulmonary edema where lung inflation creates a gradient for liquid movement from alveolar space to the extra-interstitium 1004. It is believed that moving fluids to the interstitial space will improve ventilation because removal of fluids from the alveolar region will permit improved gas exchange. An increase or normalization of lung volume or FRC may also treat OSA or CSA in patients with OSA (obstructive sleep apnea) or CSA (central sleep apnea) and thereby benefit the cardiovascular system 1005. For example, one or more devices and methods described in copending patent applications set forth above may be used to treat OSA or CSA. Increased or normalized lung volume, FRC, increased inspiration duration or elongated exhalation period all lead to reduction in average, sustained, or instantaneous intrathoracic pressures leading to improved cardiac, pulmonary, and renal pressures all simultaneously lead to reduction or prevention of pulmonary congestion.

Figure 1B:
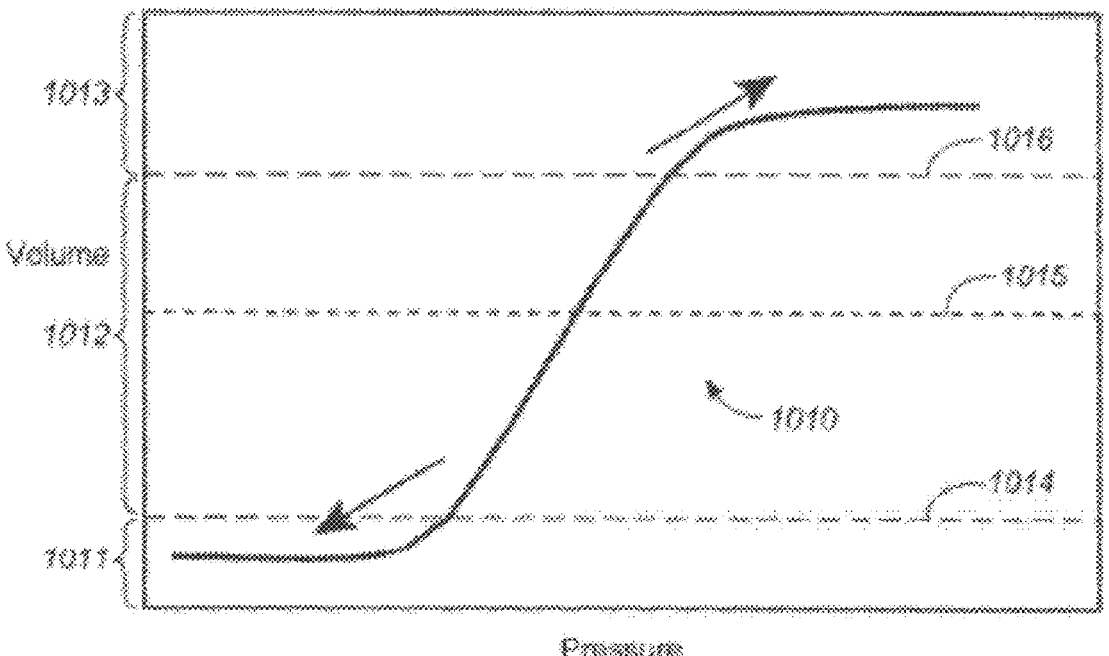
FIG. 1B is a pressure volume curve illustrating use of stimulation in accordance with an aspect of the invention.

FIG. 1B illustrates a pressure/volume curve 1010 illustrating a relationship between transthoracic pressure and lung volume. This example illustrates, among other things how stimulation may be provided to reduce breathing effort and/or intrathoracic pressure change for a given inspiration volume. At lower lung volumes 1011, a greater change in pressure is required to increase lung volume a given amount through inspiration, thus providing a greater work of breathing and thereby increasing metabolic requirements and load on heart as well. Similarly at higher lung volumes 1013, greater change in pressure and effort are required to increase lung volume through inspiration. However, in between the lower volumes 1011 and higher volumes 1013 there is a steeper portion of the curve 1012 where at a given lung volume, inspiration produces an efficient increase in lung volume with less change in pressure required to effect a given volume and therefore less effort required by the respiratory muscles to produce a given change in pressure. It is believed that an increase in required effort to breathe may result in poorer breathing or less effort and gas exchange, particularly in heart failure patients. It is also believed that greater fluctuations in intrathoracic pressure may contribute the conditions affecting heart failure. Thus in accordance with one aspect of the invention, stimulation may be provided to increase resting lung volume so that greater breathing efficiency and gas exchange is provided. Where a patient's normal resting lung volume or functional residual capacity is typically low, it may be increased. Where a patient's resting lung volume is lower than normal for a healthy individual, it may be normalized so that it is brought to a level where efficient breathing occurs. For example a low lung volume 1014 may be increased to higher lung volumes 1015 or 1016 which are at an efficient volume 1012 on the pressure volume curve 1010.

Stimulation may be provided on a sustained or intermittent basis. Stimulation may be provided when a patient is asleep or awake. In accordance with one aspect of the invention, stimulation is provided to compensate for lung volume lost at the onset of sleep or during sleep. In accordance with one aspect of the invention the stimulator may be turned on by the patient prior to sleeping or may be triggered by a sensed parameter or real time clock. A sensor may be used to sense one or more physiological parameters indicating onset or a specific stage of sleep. Other sensors may sense one or more conditions that may be used to determine appropriate times or parameters for stimulation.

In accordance with another aspect of the invention stimulation is provided to control breathing to reduce respiration rate and thereby improve, prevent or slow cardiac disease by reducing hypertension, reducing sympathetic nerve activation, providing SaO2 levels, and/or increasing cardiac output. It is believed that lowering breathing rate will provide a decrease in cardiac rate, and an enhanced vagal response.

In accordance with one aspect of the invention, breathing rate may be controlled by augmenting breathing or stimulating during intrinsic breathing to increase peak tidal volume and/or to increase inspiration duration. Increasing the duration of inspiration or tidal volume it is believed will cause the timing of the next intrinsic breath to be delayed due to the central nervous controller tendency to maintain minute ventilation in absence of any change at the chemoreceptor level. The rate may be continuously slowed by detecting each intrinsic breath and providing stimulation or augmenting until the duration of inspiration, tidal volume or exhalation rate is at a level that brings the breathing rate to a desired rate which is reduced by the central nervous control of minute ventilation.

Figures 2A, 2B, 2C:
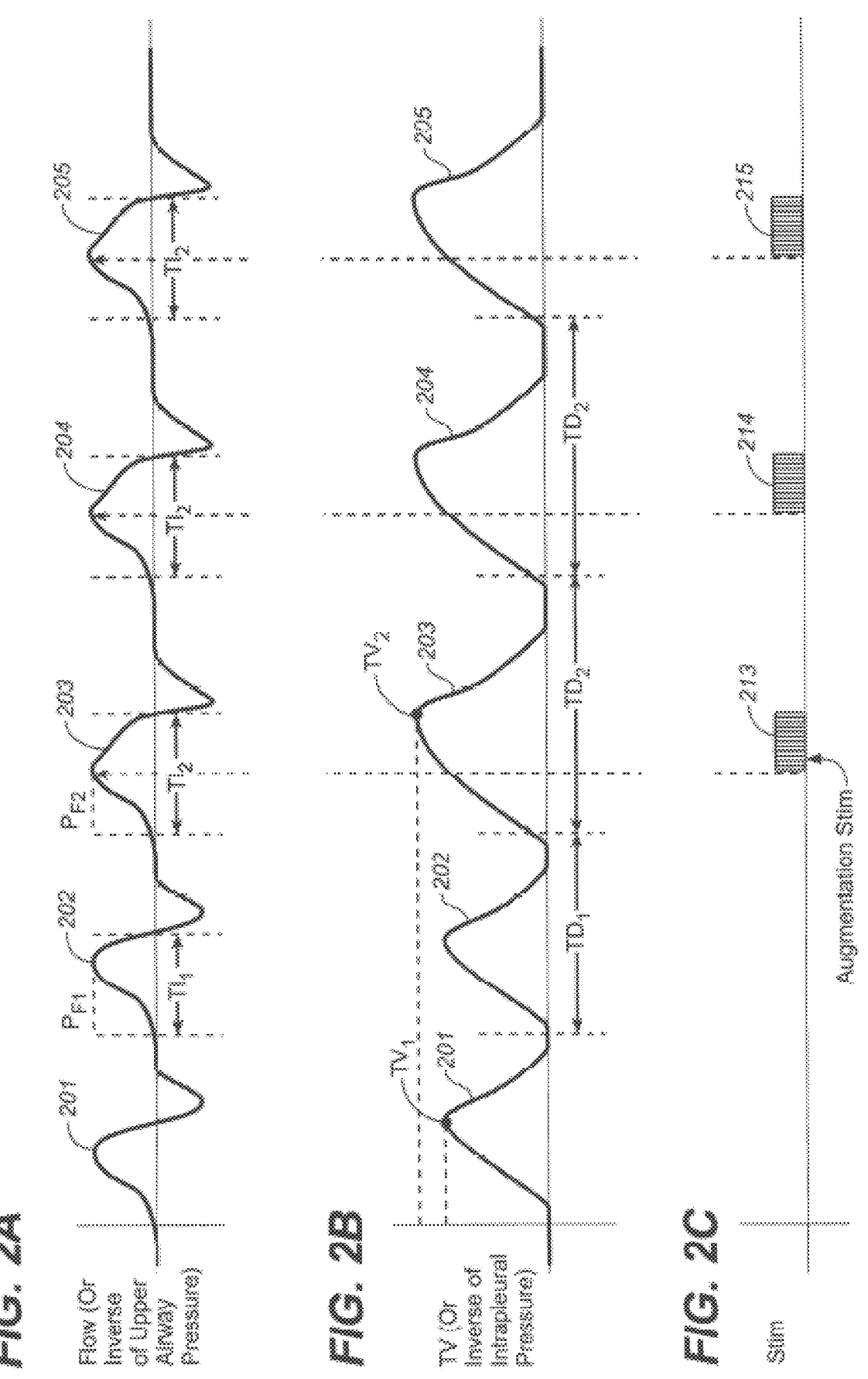
FIGS. 2A, 2B and 2C illustrate respectively, flow, tidal volume and stimulation envelope signals corresponding to use of a device and method in accordance with an aspect of the invention.

FIGS. 2A to 2C illustrate stimulation during intrinsic breathing in accordance with one aspect of the invention. FIG. 2A illustrates flow for breaths 201, 202, 203, 204 and 205. FIG. 2B illustrates tidal volume of breaths 201, 202, 203, 204, and 205. Breaths 201, 202 are intrinsic breaths. Breaths 203, 204, and 205 are intrinsic breaths that are augmented by stimulation configured to elicit a diaphragm response as illustrated schematically by stimulation markers 213, 214, and 215.

Stimulation is initiated at a period of time during inspiration and is provided for a period a time in a manner configured to increase tidal volume. Stimulation during intrinsic breathing and augmenting breathing are described in one or more related applications as set forth herein which are incorporated completely and without limitation herein by reference. The tidal volume TV2 of the breaths 203, 204, 205 where inspiration is augmented is greater than the tidal volume TV1 of the intrinsic breaths 201, 202. According to one variation, the peak flow during stimulation Pf2 may be configured as shown to be close to the peak flow Pf1 during intrinsic breathing. The inspiration duration TI1 of intrinsic breathing is shorter than the inspiration duration TI2 of augmented breaths 203, 204, 205. The duration TD1 of intrinsic breathing is increased to duration TD2 and with stimulation signals 213 214, 215, to achieve a desired rate.

In accordance with another aspect of the invention, stimulation during intrinsic breathing may be provided to inhibit or delay onset of next inspiration. According to an aspect, stimulation may be provided during exhalation to inhibit or delay onset of an inspiration thereby slowing breathing rate. According to an aspect, stimulation may be provided to extend exhalation thereby delaying the onset of a subsequent inspiration. According to an aspect, stimulation may be provided at a low energy, low level or low frequency to inhibit onset of an inspiration, thereby slowing breathing rate. Examples of low energy, low level and/or low frequency stimulation are set forth in the related applications herein.

The rate of intrinsic breathing may be controlled by delaying intrinsic breaths with low energy (for example a lower amplitude, frequency and/or pulse width than desired for paced breathing) diaphragm stimulation provided during intrinsic breathing.

According to one aspect, low energy stimulation may be provided during intrinsic breathing, delaying onset of the next breath and thereby slowing breathing rate. According to another aspect, stimulation may be initiated sufficiently prior to the onset of the next breath so as to reduce the likelihood that the stimulation would trigger a breath. A combination of lower energy stimulation and timing the stimulation sufficiently prior to the onset of the next breath may be used to slow breathing rate.

Figures 3A, 3B, 3C, 3D:
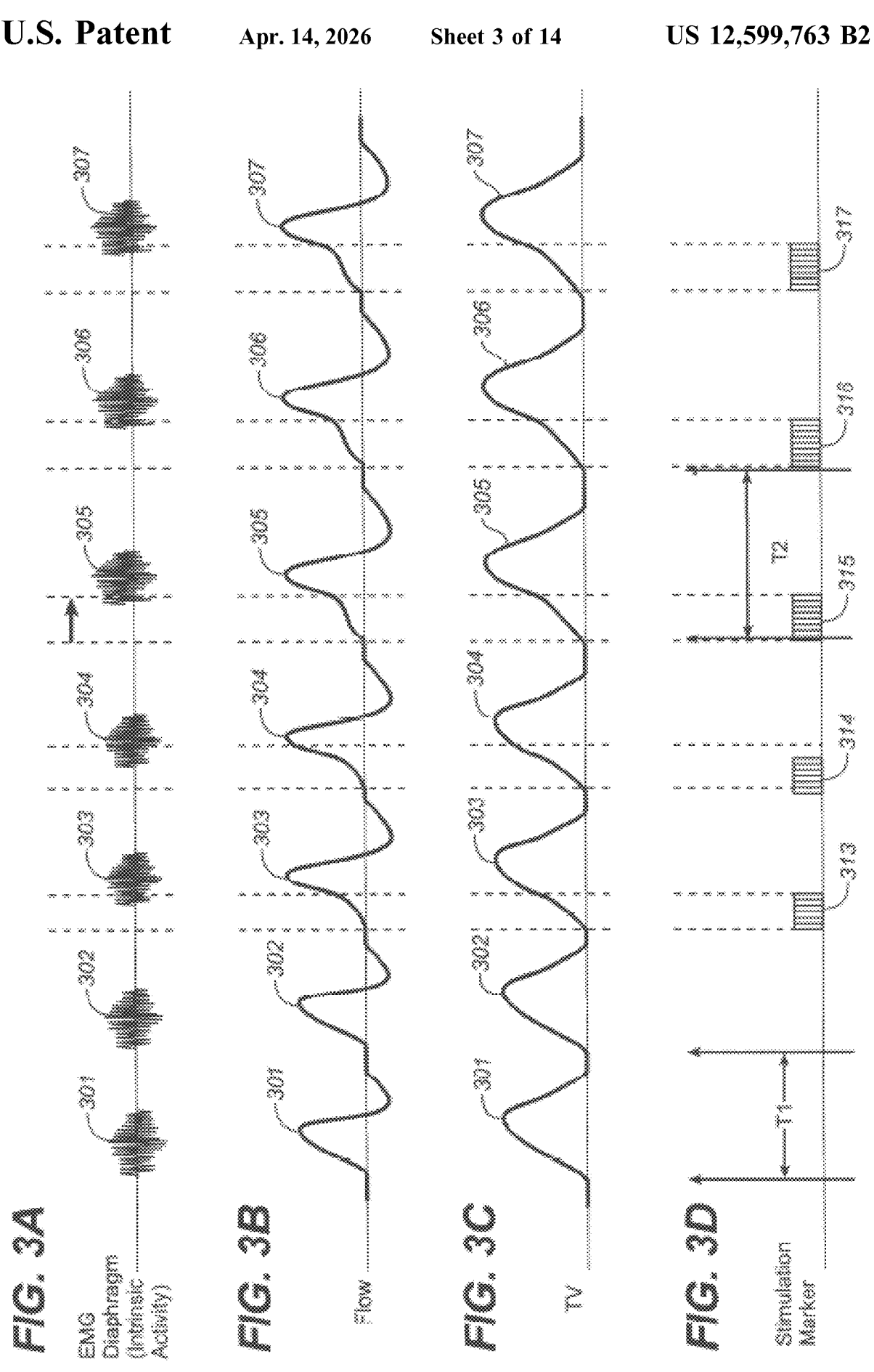
FIGS. 3A, 3B, 3C and 3D illustrate respectively, EMG, flow, tidal volume and stimulation envelope signals corresponding to use of a device and method in accordance with an aspect of the invention.

FIGS. 3A to 3D illustrate stimulation provided to slow breathing in accordance with one aspect of the invention. FIG. 3A illustrates intrinsic diaphragm EMG activity corresponding to breaths 301 through 307. FIGS. 3B and 3C respectively illustrate flow and tidal volume corresponding to breaths 301 through 307. FIG. 3D illustrates stimulation envelopes corresponding to stimulation signals 313, 314, 315, 316, and 317 provided prior to onset of breaths 303, 304, 305, 306, and 307 respectively. Stimulation 313, 314, 315, 316, 317 is provided prior to the onset of breath 303, 304, 305, 306, 307 respectively, as determined, for example, by a model that predicts the onset of breathing or by the actual detection of the intrinsic diaphragm EMG activity (FIG. 3A). Stimulation is sustained for a period of time. For example, the stimulation may be provided until the onset of the intrinsic breath is detected by the EMG or other physiological signals. As illustrated, the stimulation increases the duration of a respiration cycle T2 with respect to the duration T1 of an intrinsic breathing cycle. As further illustrated, intrinsic breathing cycles 303 to 307 may have greater flow or tidal volume to compensate for the slower breathing rate that is induced by the stimulation.

In accordance with another aspect of the invention, stimulation to increase tidal volume or inspiration duration may be provided in combination with stimulation during exhalation to inhibit or delay the onset of the next inspiration.

In accordance with another aspect of the invention stimulation may be provided to delay exhalation by stimulating at the end of inspiration at a level that slows exhalation. Such stimulation may be provided by stimulating during intrinsic breathing or by providing paced breathing for example that maintains minute ventilation while providing a slower rate of breathing.

Figures 4A, 4B, 4C:
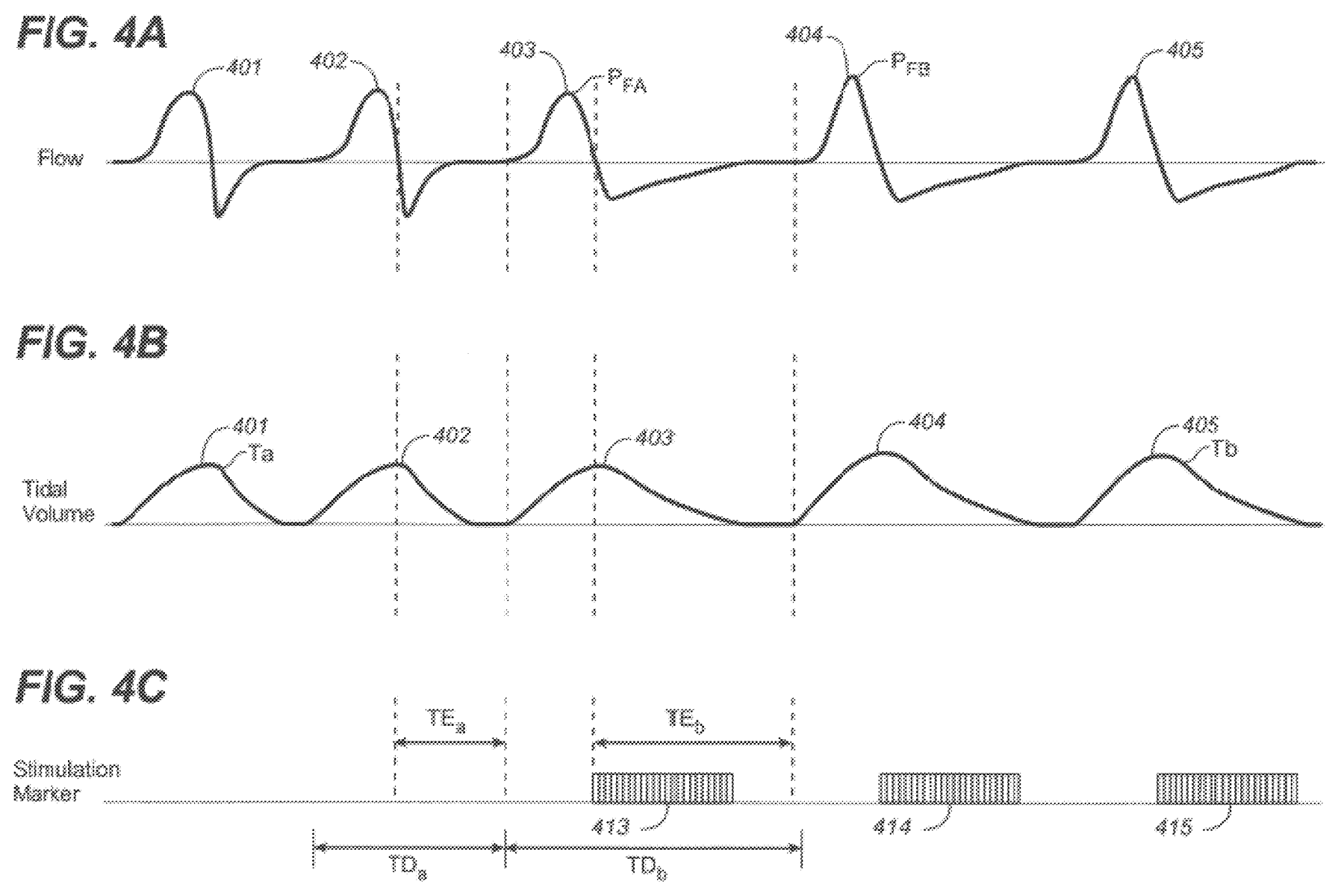

FIGS. 4A-4C illustrate stimulation during intrinsic breathing in accordance with one aspect of the invention. FIG. 4A illustrates flow for breaths 401, 402, 403, 404 and 405. FIG. 4B illustrates tidal volume of breaths 401, 402, 403, 404 and 405. Breaths 401, 402 are intrinsic breaths. Breaths 403, 404, and 405 are intrinsic breaths that are augmented by stimulation configured to elicit a diaphragm response as illustrated schematically by stimulation markers 413, 414, and 415. Stimulation is initiated at a period of time at the end of inspiration and is provided for a period a time through the exhalation period. Detection and stimulation techniques are set forth, for example in related applications hereto. Stimulation may be provided at a low energy level including at a low frequency. Stimulation during intrinsic breathing and augmenting breathing, low level and/or low frequency are described in one or more related applications as set forth herein which are incorporated completely and without limitation herein by reference. The peak flow during stimulation Pfb may be greater than the peak flow Pfa during intrinsic breaths 401, 402 as illustrated. The peak flow during stimulation Pfb may be also not be greater than the peak flow Pfa during intrinsic breaths 401, 402. Similarly tidal volume Tb is for breaths 404, 405 after stimulation 413 and 414 respectively. Such greater flow or tidal volume may intrinsically compensate for the slower breathing rate that is induced by the stimulation. It is believed that stimulation during exhalation inhibits or delays onset of inspiration. The stimulation also slows exhalation (i.e., during the period which exhalation is occurring at a relatively faster rate) so that the exhalation duration TEb during stimulation is greater than the intrinsic exhalation duration TEa. Exhalation is slowed by stimulation thus slowing the overall rate of breathing. The duration of the intrinsic breathing respiration cycle TDa is increased to duration TDb during stimulation, thus reducing the breathing rate to a desired rate.

Stimulation may also be provided to slow or control breathing rate in a manner that provides a paced breath with controlled exhalation as illustrated for example in U.S. patent application Ser. No. 10/966,474, filed Oct. 15, 2004 and U.S. patent application Ser. No. 10/966,472, filed on Oct. 15, 2004.

Figures 5A, 5B, 5C:
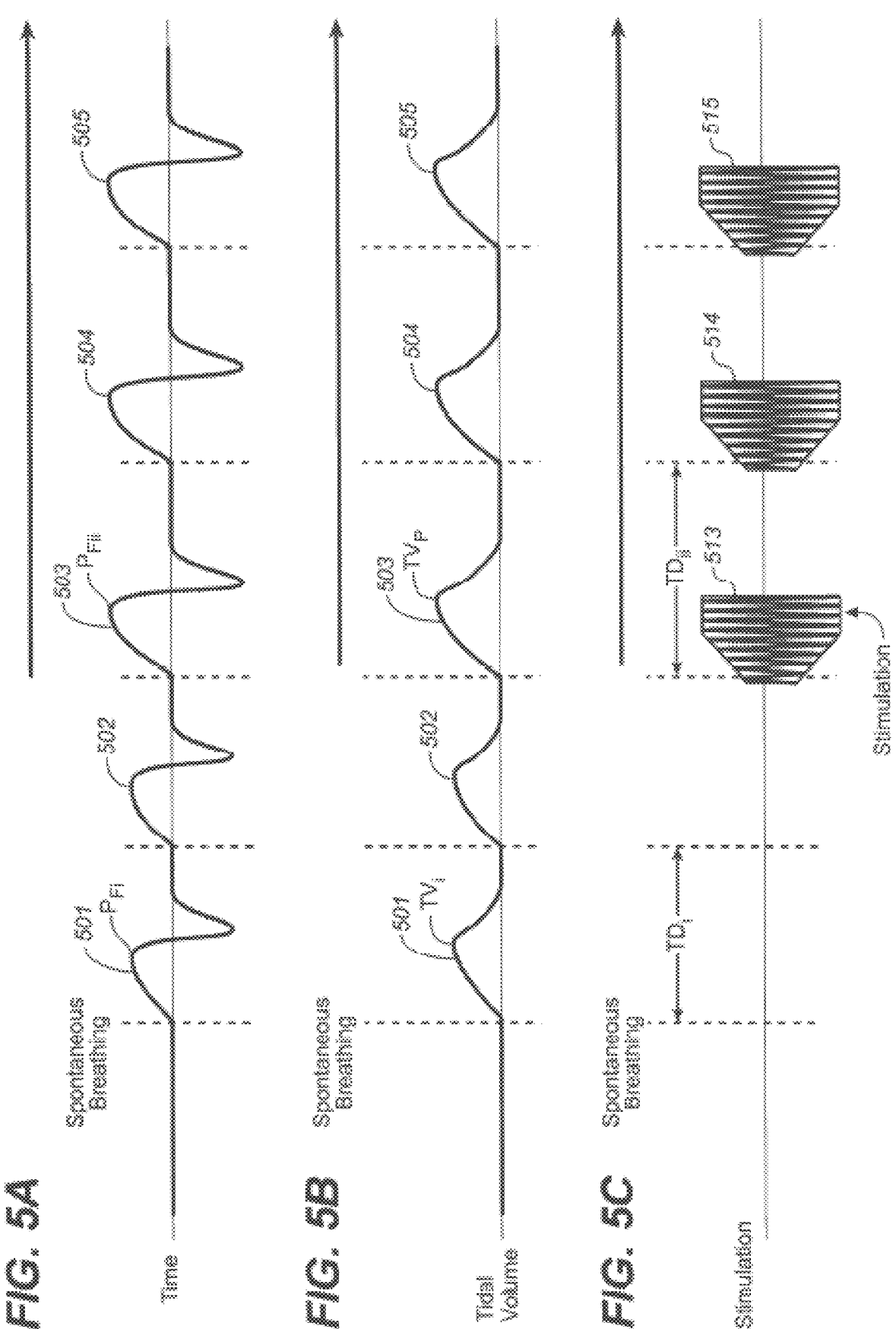
FIGS. 5A, 5B, and 5C illustrate respectively, flow, tidal volume and stimulation envelope signals corresponding to use of a device and method in accordance with an aspect of the invention.

FIGS. 5A to 5C illustrate stimulation used to control breathing and breathing rate in accordance with the invention. Breaths 501 and 502 are intrinsic breaths occurring at a rate such that the duration of the respiration cycle is TDi and having tidal volume TVi and peak flow PFi. Breaths 503, 504 and 505 are paced breaths with higher tidal volume TVp and peak flow PFp. Peak flow PFp may be controlled to be at a level substantially the same as, higher, or lower than intrinsic peak flow. Paced breathing is provided in a manner in which breathing is controlled or taken over by stimulated breathing. Examples of techniques for controlling breathing, respiratory drive and/or taking over breathing are set forth in related applications incorporated completely and without limitation herein by reference. In general greater tidal volume permits a reduction in breathing rate or an increase in duration of breathing cycle to TDii while maintaining minute ventilation. FIG. 5C illustrates stimulation envelopes 513, 514, 515 respectively corresponding to stimulated breaths 503, 504, 505.

In accordance with another aspect of the invention stimulation is provided to control minute ventilation to therapeutically affect blood gas levels. Examples of controlling minute ventilation are set forth for example in U.S. patent application Ser. No. 10/966,474. Such stimulation may be provided, for example, during sleep to thereby increase or normalize SaO2 levels during sleep. In accordance with one aspect of the invention minute ventilation is controlled to normalize SaO2 levels while not decreasing PaCO2 levels close to the apneic threshold. According to this aspect minute ventilation may be actively controlled using sensors to sense SaO2 or PaCO2 levels. Weaning off of pacing may be desirable to insure that the intrinsic drive to breath is still present. Paced breathing may be calibrated, for example at implant or adjusted during device use, so that the device is able to provide the appropriate minute ventilation at each pacing setting. This information may be obtained for example through sleep studies where the device is designed to provide stimulation during sleep.

In accordance with another aspect of the invention, stimulation is provided to create a deep inspiration or an increased tidal volume to thereby reduce sympathetic nerve bias, improve blood gas levels, stimulate reflexes (for example the Hering-Bruer reflex related to activating stretch receptors), increase lung volume, normalize or reset breathing (one or more parameters) or provide other beneficial therapies to improve cardiovascular function or heart failure condition.

Examples of creating deep inspiration are set forth in U.S. patent application Ser. No. 11/272,353 filed Nov. 10, 2005. While these examples refer to using deep inspiration to treat apnea, similar techniques for stimulation may be used to create deep inspiration breaths for improving cardiovascular function or treating heart failure. Stimulation may be provided during intrinsic inspiration or in between inspiration cycles.

In accordance with another aspect of the invention stimulation may be provided to manipulate intrathoracic pressure to thereby produce a therapeutic effect.

According to one embodiment, stimulation is provided to reduce intrathoracic pressure through induced contraction of the right and/or left hemidiaphragm. It is believed that for some patients, reduction in intrathoracic pressure may have a beneficial effect on the patient's cardiovascular function or condition. For example, a reduced intrathoracic pressure may increase stroke volume at least in part through a decrease in central venous pressure; and reduce pulmonary arterial and wedge pressures in relation to atmospheric. A reduced intrathoracic pressure may also provide a decrease in filling pressure in the right ventricle and may also thereby improve systemic venous return. A reduced intrathoracic pressure may also provide better coronary artery perfusion.

In accordance with one aspect of the invention, patients with heart failure manifesting in poor ventricular filling may be treated with stimulation to reduce intrathoracic pressure. In accordance with one aspect of the invention, patients with diastolic heart failure may be treated with stimulation to reduce intrathoracic pressure. In accordance with another aspect of the invention stimulation to reduce intrathoracic pressure may be provided to patients who are hypovolemic where the therapeutic effects of improved ventricular filling and venous return would be particularly beneficial.

According to one aspect of the invention stimulation is provided to elicit a diaphragm response to cause a reduced intrathoracic pressure. The stimulation is provided at a level that does not elicit a breath, in other words, where intrinsic breathing continues to occur. Examples of stimulation such as bias stimulation and low energy or low frequency stimulation are described in related applications set forth herein. The stimulation eliciting a reduced intrathoracic pressure may be sustained or intermittent. Stimulation is preferably provided when a patient is sleeping but may also be provided when a patient is awake.

In accordance with one aspect of the invention, stimulation may be provided to one hemidiaphragm to elicit a more impactful change in intrathoracic pressure in the respective side of the thoracic cavity. For example the right hemidiaphragm may be stimulated in such a way to cause a reduced intrathoracic pressure primarily in the right thoracic cavity to thereby effect the right side of the heart to a greater degree than the left. Or stimulating unilaterally on the diaphragm may serve to minimize the pressure changes that the heart is exposed to. This may be beneficial when an increased lung volume is desired to treat OSA or CSA. Sensors may be used to sense arterial and venous blood volume so that stimulation may be adjusted based on patient's blood volume state. For example, stimulation may be increased or turned on when the patient is in a hypovolemic state where in a particular patient a greater benefit would be produced with a more negative intrathoracic pressure. Such sensors may include, for example, impedance (plethysmography) sensors used to monitor fluid levels in the body. Separate electrodes, or existing stimulation electrodes may be used in a configuration or with frequencies that can determine resistance and/or reactance. Fluid volume changes may, for example, be monitored based on a baseline established with the sensors and a hyper or hypo volemic state may be detected. A list of possible sensors are described in the references above.

In accordance with another aspect of the invention, stimulation is provided to elicit a diaphragm response that improves heart failure as described above in combination with treating sleep disorders that contribute to or worsen heart failure. Accordingly, stimulation is provided as described in the related patent applications set forth herein, to elicit a diaphragm response to thereby reduce breathing disorders to thereby improve condition of a heart failure patient. One or more specific methods of reducing sleep disordered breathing events and preventing sleep disordered breathing are described in related applications as set forth herein. In accordance with one aspect of the invention, stimulation is provided prior to a physiological trigger of a central or obstructive sleep apnea event in a manner that reduces the occurrence of such events, thus reducing the effects of apnea events that worsen heart failure.

In accordance with another aspect of the invention a combined cardiac rhythm management device and diaphragm/phrenic nerve stimulation device is provided to provide an enhanced combined treatment device. In accordance with this aspect of the invention, the diaphragm stimulation element may comprise an abdominally placed stimulator positioned on the diaphragm or phrenic nerve, a thoracoscopically placed stimulator positioned on the diaphragm or phrenic nerve, a phrenic nerve stimulator positioned in the neck region on or adjacent the phrenic nerve (transcutaneous, percutaneous, or otherwise implanted); transcutaneous stimulation of the diaphragm through leads at or near the ziphoid region (this may be in combination with a defibrillator function or device that is configured for subcutaneous stimulation of the heart); or a pectorally positioned lead, for example, placed transvenously in a vein or artery in proximity of one or both phrenic nerves.

The system may be further enhanced through the ability to avoid negative device/device interactions where a separate controller is used, e.g. for a CRT, pacemaker, ICD or other therapeutic electrical stimulation device. The system may also provide arrhythmia and sleep disorder detection algorithms through sensing of both the cardiac and respiration cycles.

The system may also be included in a combination with a CRM device having a common controller.

Additionally, the system may also be utilized to provide a continuous or synchronized low level stimulation to the phrenic nerve or diaphragm overlapped with the patient's own intrinsic breathing to reduce an intrathoracic pressure and improve cardiac output. The patient's SaO2 levels may also be improved and the heart and respiration rates may be reduced.

This may be achieved in part by sensing and/or monitoring the patient's intrathoracic pressure levels and applying the continuous or synchronized stimulation, as described herein, to reduce or alleviate the patient's elevated intrathoracic pressure. In applying the stimulation to the patient's phrenic nerve or diaphragm, any of the sensing and stimulation devices and methods described in the following may be utilized for applying the continuous or synchronized low level stimulation: U.S. Patent Application Ser. Nos. 61/893, 404 filed Oct. 21, 2013; 60/925,024 filed Apr. 18, 2007; Ser. No. 13/598,284 filed Aug. 29, 2012; Ser. No. 12/082,057 filed Apr. 8, 2008; Ser. No. 12/082,057 filed Apr. 8, 2008; Ser. No. 12/069,823 filed Feb. 13, 2008; Ser. No. 12/044,932 filed Dec. 21, 2007; Ser. No. 11/981,342 filed Oct. 31, 2007; Ser. No. 11/480,074 filed Jun. 29, 2006; Ser. No. 11/271,315 filed Nov. 10, 2005; Ser. No. 11/271,554 filed Nov. 10, 2005; Ser. No. 11/271,353 filed Nov. 10, 2005; Ser. No. 11/271,264 filed Nov. 10, 2005; Ser. No. 11/480,074 filed Jun. 29, 2006; Ser. No. 11/271,726 filed Nov. 10, 2005; Ser. No. 10/966, 487 filed Oct. 15, 2004; Ser. No. 10/966,484 filed Oct. 15, 2004; Ser. No. 10/966,474, filed Oct. 15, 2004; Ser. No. 10/966,421 filed Oct. 15, 2004; Ser. No. 10/966,472 filed Oct. 15, 2004; Ser. No. 10/686,891 filed Oct. 15, 2003. Each of these applications is incorporated completely and without limitation herein by reference for any purpose.

Recent sensors and blood pressure and impedance sensing technologies have proven detecting worsening of heart failure as discussed in the Appendix below. The Appendix is incorporated herein by reference in its entirety for any purpose. A majority of these sensors monitor blood pressures within the pulmonary artery, right ventricle, left atrium, intrathoracic, or utilizing ventricular contractions or thoracic impedance to measure and monitor changes that could lead to heart hemodynamics decompensation or worsening and eventually hospitalization. These devices generally transmit a wireless signal through the sensor or a device that they are attached to the patient or caregiver for intervention that incudes medication therapy or lifestyle or physician visit. However, none of these sensor technologies have offered a real-time therapy within the implantable device to improve cardiac output and also reduce intrathoracic, pulmonary, or cardiac pressures.

As described in the Appendix and herein, the implantable devices also include at least one phrenic nerve or diaphragm stimulation lead or electrodes to deliver therapy either reactively (in response to sensors and programmed parameters outcome) or proactively as determined duty cycle of a patient-induced event. Upon detection of an increase in pressures, the device may deliver stimulation in such a manner to reduce intrathoracic pressure and related pulmonary and cardiac pressures. Such therapy is expected to reduce pulmonary congestion and dyspnea in heart failure patients.

Another application of this device/technology is to improve cardiac hemodynamics by increasing venous return and cardiac output.

Another application of this technology includes applying negative pressure therapy even in the absence of increased pressures and to improve cardiac output and off-loading the heart. In the long-term, the heart could remodel and improve contractility on its own.

The implantable sensor could receive energy from outside the body such as the CardioMEMS pulmonary pressure sensor and then receive commands to stimulation phrenic nerve to reduce pressures and increase cardiac output. The stimulation electrodes could be also activated from outside the body.

Another application of this device is treating central and obstructive sleep apnea as described in further detail in the patent applications incorporated hereinabove.

Such devices could also synchronize its stimulation of the phrenic nerve to cardiac cycles such systole or diastole. However, in order to achieve sustained reduction in pulmonary or atrial pressures, a sustained stimulation that is synchronized to respiration cycles and also cardiac cycles may be provided. Intrathoracic pressure is lowest at the peak of inspiration and therefore while it is possible to stimulate, the stimulation applied toward the end of inspiration and/or part of or the entire exhalation phase may be more efficient.

The stimulation algorithm could be targeted toward multiple benefits/targets. At the time of device implant, the algorithms for each target could be titrated and thresholds could be established per patient:

1. Proactive stimulation during sleep or awake to increase cardiac output in diastolic or systolic heart failure patients;
   a. Device will self-adjust stimulation relative to the need for certain cardiac output increase;
2. Responsive therapy where the device monitors pressures or cardiac and intrathoracic impedances or cardiac output and therefore responds to need to reduce intrathoracic pressure;
3. Responsive device to increase cardiac output;
4. Responsive device to increase lung volume;
5. Integrated with any CRM device; pacemaker, defibrillator, cardiac resynchronization therapy (CRT);
6. Integrated with other heart failure devices such as vagal nerve stimulation or others;
7. Integrated with sleep apnea therapy devices including hypoglossal nerve stimulation devices.
8. Responsive therapy device to improve kidney function or improve GFR
9. Responsive device to reduce pulmonary pressures and pulmonary congestions In one example, because the algorithms for each target are able to be titrated, the phrenic nerve or diaphragm tissue may be stimulated to cause a titratable diaphragm contraction such that an initial pressure within a thoracic chamber is reduced. In another example, the phrenic nerve or diaphragm tissue may be stimulated to improve a cardiac output in titratable manner as well.

In stimulating the phrenic nerve or diaphragm as well as monitoring the patient's intrathoracic pressure, as described herein, the electrodes may be utilized in combination with or integral to a cardiac lead. Such electrodes are described in further detail in U.S. Patent Application Ser. No. 61/893,404 filed Oct. 21, 2013, which has been incorporated by reference hereinabove in its entirety and for any purpose.

The mapping and neurostimulation electrodes presented herein are intended to be used in conjunction with or integral to a cardiac lead. They could also be an independent lead. The mapping electrodes mounted on the sleeve is intended to traverse the cardiac lead, provide specificity to specific neural activation points within the vascular structure where neural anatomy resides adjacent to the vascular structure, such as the phrenic or vagus nerve. Once the targeted nerve anatomy is identified by the mapping electrodes, the neurostimulation electrodes can be arranged or deployed within the vascular structure and adjacent to the neural anatomy such that the electrodes provide the desired neurostimulation therapy.

Figure 6:
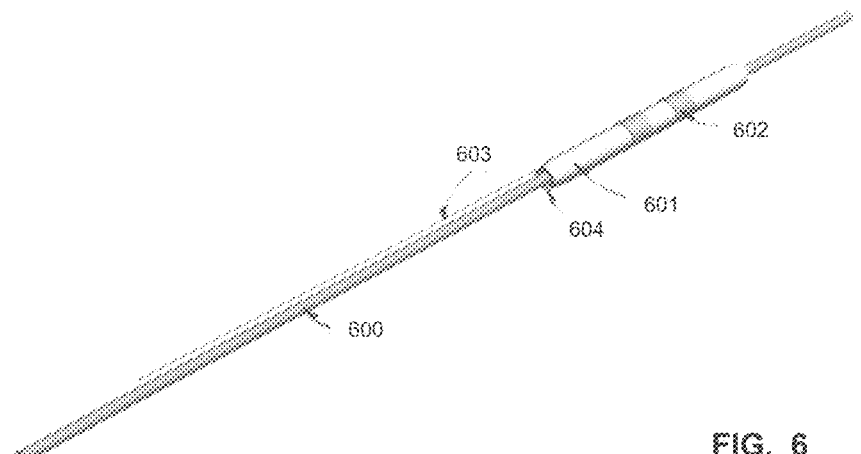
FIG. 6 is an isometric view of a mapping electrodes mounted on a mobile sleeve which is descending over a cardiac lead.

FIG. 6 illustrates an embodiment of a mapping sleeve 601 that includes at minimum one but in this embodiment plural mapping electrodes 602, traversing a cardiac lead 600. The mapping sleeve 601 in this embodiment is inserted over the cardiac lead 600 at the proximal end of the lead and advanced along the cardiac lead body to a position in which the mapping electrodes 602 are arranged to activate neural anatomy.

The mapping sleeve 601 may be constructed of a bio-stable polymer, silicone rubber, or other insulation materials suitable for isolating a plurality of electrodes. The mapping electrodes 602 may be constructed of platinum or platinum alloys but in other embodiments constructed of any bio-stable conductor, titanium, palladium, stainless steel, carbon, or similar materials, alloys. or composite materials.

Figure 7:
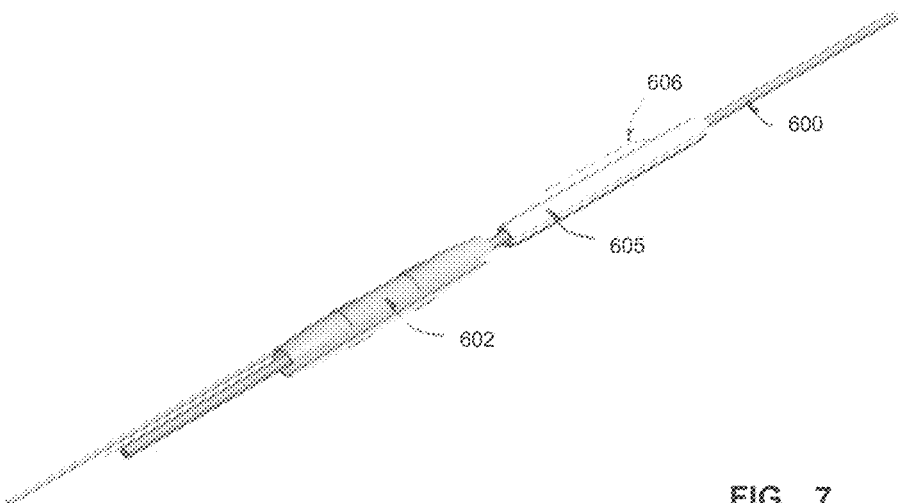
FIG. 7 is an isometric view of a mapping electrodes mounted on a mobile sleeve which is descending over a cardiac lead and includes deployed neuro-stimulation electrodes.

Once the neural anatomy is identified within the vascular structure, the mapping sleeve 601 is retracted as illustrated in FIG. 7 exposing an inner sleeve 605 that includes an expanding wire member 606. The wire member may be constructed of any bio-stable compliant metal, nitinol, stainless steel, titanium alloys, or plastic material suitable to expand into position.

Figure 8:
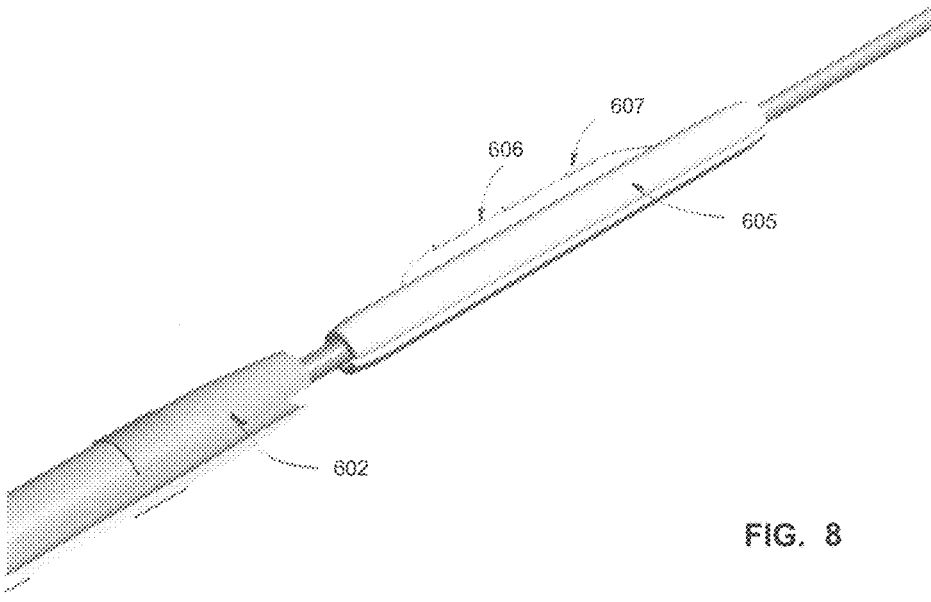
FIG. 8 is an enlarged isometric view of mapping electrodes mounted on a mobile sleeve including neuro-stimulating electrodes deployed on an expandable wire member.
Figures 9A, 9B, 9C:
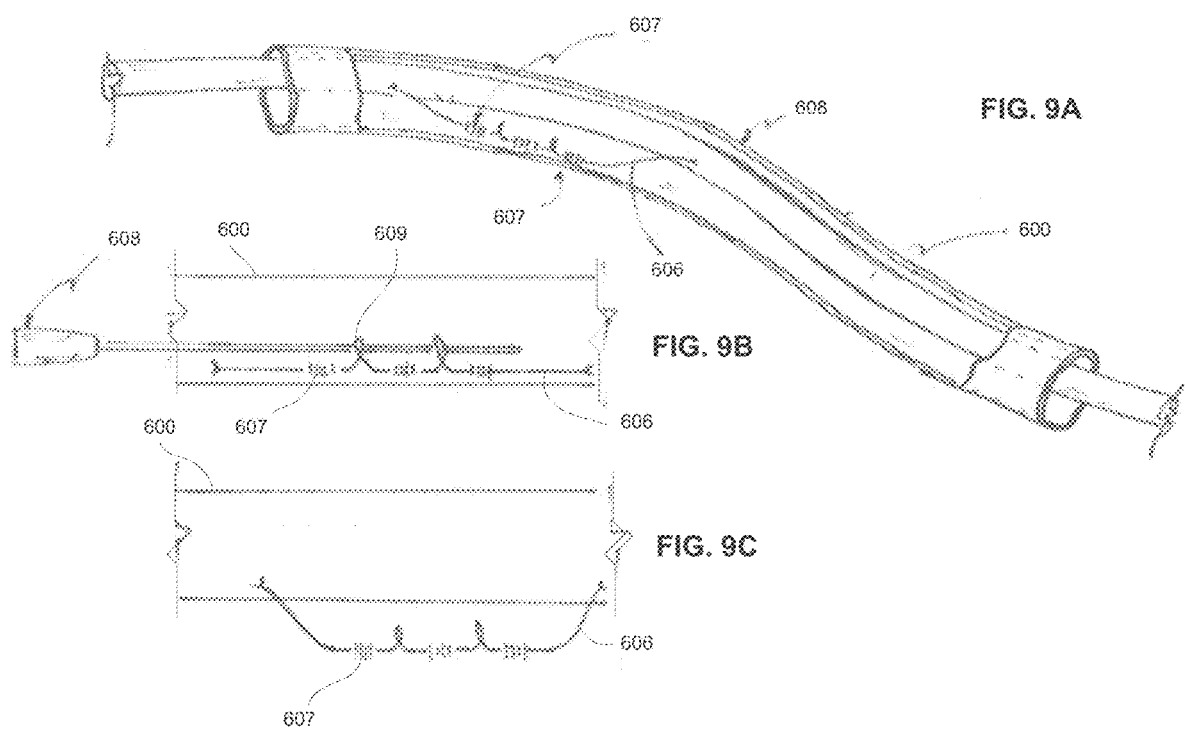
FIG. 9A is an exemplary side view of a neuro-stimulation electrode deployed, e.g., in a subclavian vein.
FIGS. 9B and 9C show detail side views of one mechanism for deploying the electrodes.

As illustrated in FIG. 8, the expanding wire member 606 in which carries at least one but in the preferred embodiment, plural neurostimulating electrodes 607. The expanding wire member 606 when in the un-deployed state, resides under the mapping sleeve so that the entire assembly can negotiate the vascular structure. The wire 606 may be retained in its low-profile configuration through various mechanism, such as a stylet 608 which may be passed through one or more retaining loops 609 defined along the wire 606, as shown in the detail view of FIG. 9B. When deployed, the stylet 608 may be retracted such that the expanding wire member 606 expands, as shown in the detail view of FIG. 9C, to apply the neurostimulation electrodes 607 against the vascular wall, as shown in FIG. 9A. In this example, the lead 600 may utilize a IS-1 type connector.

Figure 10:
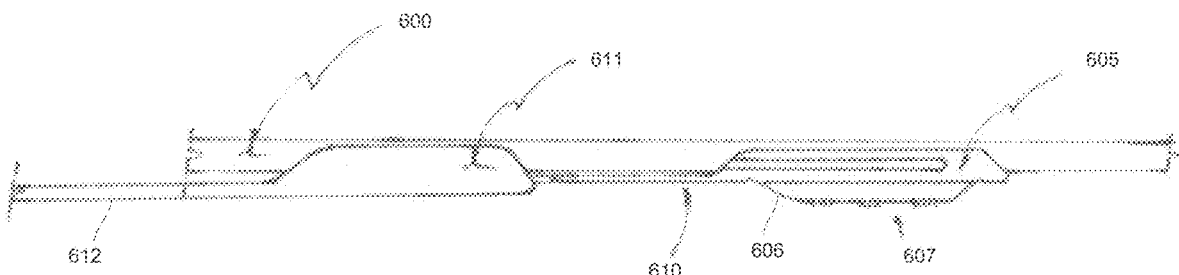
FIG. 10 is a detailed side view of a neuro-stimulation electrode.

FIG. 10 illustrates an embodiment of the deployed neurostimulation electrodes 607 expanded to reside coincident to the vessel wall 608. In the primary embodiment, the electrode wire 606 containing the neurostimulation electrodes 607 have expanded to focus the electrodes 607 current towards the neural anatomy residing outside the vascular structure. In this variation, the electrode wire 606 and electrodes 607 may be attached or coupled to a conductor cable 610. A push sleeve 611 may be slidingly positioned proximally or distally of the electrode 607 with a proximal end of the push sleeve 611 being coupled to a push rod 612. During lead insertion and intravascular delivery, the pushing sleeve 611 may remain over the wire 606 and electrodes 607. When the electrodes 607 are in position relative to the tissue wall, the push rod 612 may be actuated proximally or distally relative to the lead 600 such that the push sleeve 611 is moved to expose the wire 606 and electrodes 607 which may then be deployed as the sleeve 611 is, e.g., retracted.

The mapping electrode may be advanced down a previously implanted cardiac lead body to a point in which neural structure intersects the vascular structure. The mapping electrode is used to identity "map" the optimal stimulation location or optimal location to place the neurostimulation electrodes within the vascular structure.

Once the optimal stimulation location is identified using the mapping electrodes, the neurostimulation electrodes are deployed such that the neurostimulation electrodes are positioned in a location to energize the targeted neural anatomy.

A method of mapping or identifying the nerve is developed where once the electrode is near proximity of the nerve, stimulations of variety of frequencies and amplitude will be applied in certain sequence for optimum nerve location. The physiological response to mapping procedure will be monitored and recorded. Once the electrode is in optimum location, the electrode location in reference to other anatomical landmarks are noted and the electrode is secured. In case of mapping the phrenic nerve, several physiological parameters including diaphragm movement and response, flow, tidal volume, lung volume, minute ventilation, upper airway muscle activity, and similar parameters as it relates to respiratory parameters will be monitored in order to identify the optimum electrode placement in reference to the phrenic nerve.

A neurostimulation lead system may be comprised of a commercial lead mounted and connected to a flexible frame fabricated from nitinol or other biocompatible material where the frame may be inserted and advanced via flexible catheter body through a vessel into proximity of a nerve to be stimulated. The frame can be constructed of nitinol wires where the nitinol wires act as a "guidewire" which can be inserted through a lumen. Alternatively, the lead can be placed and fastened to the frame such that as the frame expands, the lead may adhere to the vessel wall in the intended position where the lead is facing the targeted nerve through the vessel. The frame and lead system may be housed or inserted inside a sheath or mapping sheath. Specific markers and labels on the sheath and sheath catheter may provide orientation of the lead and electrodes in reference to the targeted nerve. As the sheath is pulled away (e.g., pulled proximally), the nitinol frame may slowly expand in the intended location within the vessel and orientation relative to the nerve to be stimulated. The frame/lead system can also be collapsed by pushing the sheath distally over the frame and repositioned and released again and/or removed from the vessel.

The lead system including the frame/holder/tray may be constructed in such a way to hold more than one neurostimulation leads in symmetrical or asymmetrical positions. The frame's distal end could be one or multiple nitinol wires apposing to the vessel wall connected to each other or extending open like a regular stent. It is preferred to allow blood flow in the vessel as least interrupted as possible. In one variation, if the nitinol wires are connected to each other at the distal end, it is preferred they will be oriented against the vessel wall and not in the middle of the vessel. If the nitinol wires are not connected to each other or the tray, they should be apposed against the vessel wall in such a way to minimize vessel wall injury or perforation. The vein walls are highly complaint while the blood flow is of lower velocity. Design considerations should take into account to minimize vessel wall injury and perforation. The leads may have, e.g., 2-4 electrode contacts, where two are selected for threshold and nerve activation purposes. If two leads each with, e.g., three electrodes, are placed asymmetrically on the side of the vessel wall in proximity to the nerve to be stimulated, this configuration may allow for the selection of the best electrode pairs from both leads or just one lead. In case of slight lead migration, endothelization, or changes to lead-tissue interface impedance overtime, another set of electrodes can be selected for optimum performance. There is a possibility more than one electrode is configured as a single pole to increase the area of stimulation, for example, targeting the nerve with three electrodes instead of two and increasing the area of stimulation.

With the electrode deployed within the vessel and oriented to stimulate an adjacent nerve or nerves of interest, a treatment may be initiated by applying stimulation through the electrodes which may pass through the vessel wall and into the targeted nerve or nerves. Parameters including current, power, pulse width, timing, etc. may be varied for treating various conditions. Various treatments to be applied may include electrical stimulation for treating or mitigating conditions such as breathing disorders and/or sleep-related breathing disorders where treatment parameters which may be implemented by the electrode systems described herein are described in further detail in the following references, each of which are incorporated herein by reference in its entirety: U.S. Pat. Nos. 8,467,876; 8,255,056; 8,412,331; 8,200,336; 8,348,941; 7,970,475; 9,259,573; 8,140,164; 8,116,872; 9,370,657; 8,265,759; 10,857,363. Other examples of treatments which may be applied via the electrode systems described herein are described in further detail in the following references, each of which are incorporated herein by reference in its entirety: U.S. Pat. Nos. 8,244,358; 7,979,128; 8,160,711; 8,335,567; 8,280,513; and U.S. Pub. 2021/0060342A1.

In one variation of the electrode system, the leads may be removed after chronic implantation within the body of the patient. The nitinol frame may be coated with a biocompatible material such as silicone to prevent endothelialization. The frame may be fabricated from a biocompatible polymer such as polyether ether ketone (PEEK) and optionally coated with a material such as an anti-thrombolytic (e.g., Hemo-LAST™, AST Products, Inc., MA). The entire frame and lead may be collapsed and removed after a period of time such as up to a year. A position of the lead may be maintained by designing the spring force of the nitinol to be low enough to expand against the vessel wall but not create enough force to erode its way through the tissue. The nitinol frame could be made of one diameter nitinol tube and be fitted into variety of vessel diameters or be made of variety of nitinol tube diameters and during the procedure with the aid of imaging, e.g., ultrasound imaging, the optimal size and fit lead system can be selected and deployed after the vessel diameter is measured with the aid of imaging, such as ultrasound.

In another variation, the lead may be non-removable after chronic implantation. In this case, the nitinol frame may be endothelialized within the vessel wall after a period of time, such as thirty days or longer.

Whether the leads are removable or intended to remain within the patient, either version of the leads may be removable acutely and up to, e.g., thirty days of implantation. Furthermore, the implantation and/or treatment procedure may allow for the addition of adjunct procedures utilizing devices such as catheters, interventional devices, pacer leads, etc.

FIG. 11A shows a side view of an endovascular lead apparatus 1100 having an elongated body with a mapping sheath 1102 or catheter having one or more active electrodes 1104 placed thereon as discrete electrodes separated from one another along a length of the mapping sheath 1102. While two electrodes 1104 are illustrated in FIG. 11A, other variations can incorporate a single electrode or more than two electrodes in other configurations. The electrodes 1104 can be spaced apart at varying distances, as described in more detail below.

The apparatus 1100 may be introduced and advanced through the patient body intravascularly to position the apparatus into proximity of the nerve to be treated. Upon advancement and delivery to a target site, the electrodes 1104 can be actuated to deliver a treatment stimulation to the target site via an energy source. The treatment stimulation can be used to confirm a location of the nerve body to be treated in proximity to the vessel. The sheath 1102 can also be slowly moved towards the proximal portion 1106, thus allowing an expandable scaffold which may deploy from a low-profile delivery configuration to an expanded deployment configuration into contact against the inner walls of the vessel. One example is shown illustrating a nitinol frame 1110 coupled to an inner member and extending in its deployed configuration from a distal opening in the distal portion 1108 of the sheath 1102, as shown in FIG. 11B. The expandable scaffold may be entail any number of deployable scaffolds so long as the scaffold is deliverable in a low-profile and then deployed in an expanded configuration into contact against the interior vessel walls.

As shown in one example in FIG. 12, the sheath 1102 can be inserted into the subclavian vein and advanced intravascularly until the electrodes 1104 are positioned into proximity to, e.g., the phrenic nerve which crosses behind the subclavian vein. To confirm the treatment location, a pulse generator located externally of the patient or implanted within the patient body may be actuated such that the electrical stimulation is delivered from the controller and through the length of the sheath 1102 and to the electrodes 1104 along the mapping sheath 1102 such that the electrical stimulation passes through the vessel wall and into the phrenic nerve. When nerve capture is detected through observation or measurement of the patient's diaphragm contraction or a respiratory parameter, the electrical stimulation may be halted.

Figure 13:
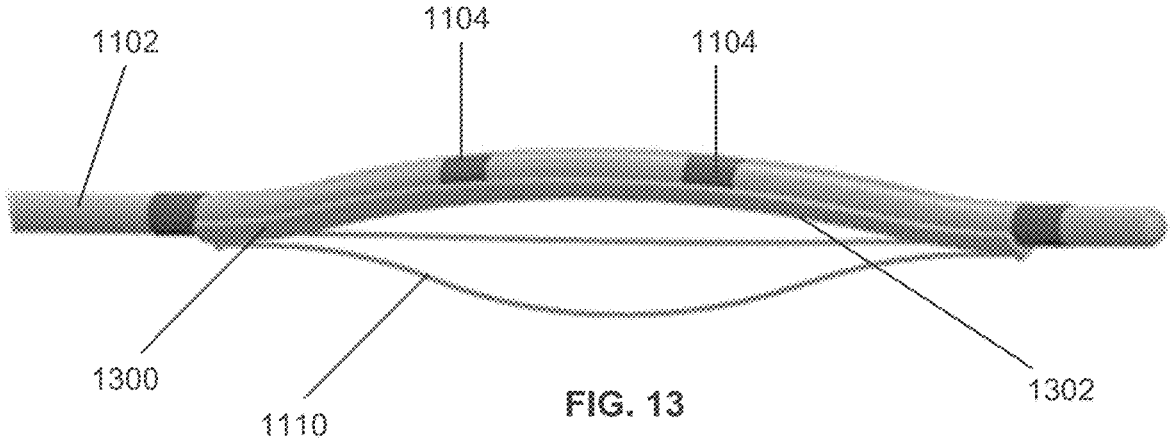
FIG. 13 shows a neurostimulation lead loaded onto a nitinol frame/tray.

FIG. 13 shows another variation of an expandable scaffold in nitinol frame 1110 which may be deployed from a mapping sheath 1102 or catheter. In this embodiment, a tray 1300 or holder positioned along a second side of the distal portion opposite to the first side can be provided to position a frame 1110 such as a nitinol frame. The electrodes 1104 may be positioned along the first side of the sheath 1102. The tray 1300 can be placed on one side of the apparatus 1100 and can comprise a channel 1302 in which the frame 1110 can sit in a low-profile delivery configuration. When the frame 1110 is ready to be deployed within the vessel, an expansion mechanism coupled to a proximal end of the one or more frame members can be actuated to transition the frame into an expanded, deployed configuration, as seen in FIG. 13. The sheath 1102 can flexibly bend in the expanded configuration while the frame 1110 may extend from the second side and also press against an interior of the vessel wall and urge the first side of the distal portion 1108 and the electrodes 1104 into contact against an inner surface of the vessel.

Figure 14:
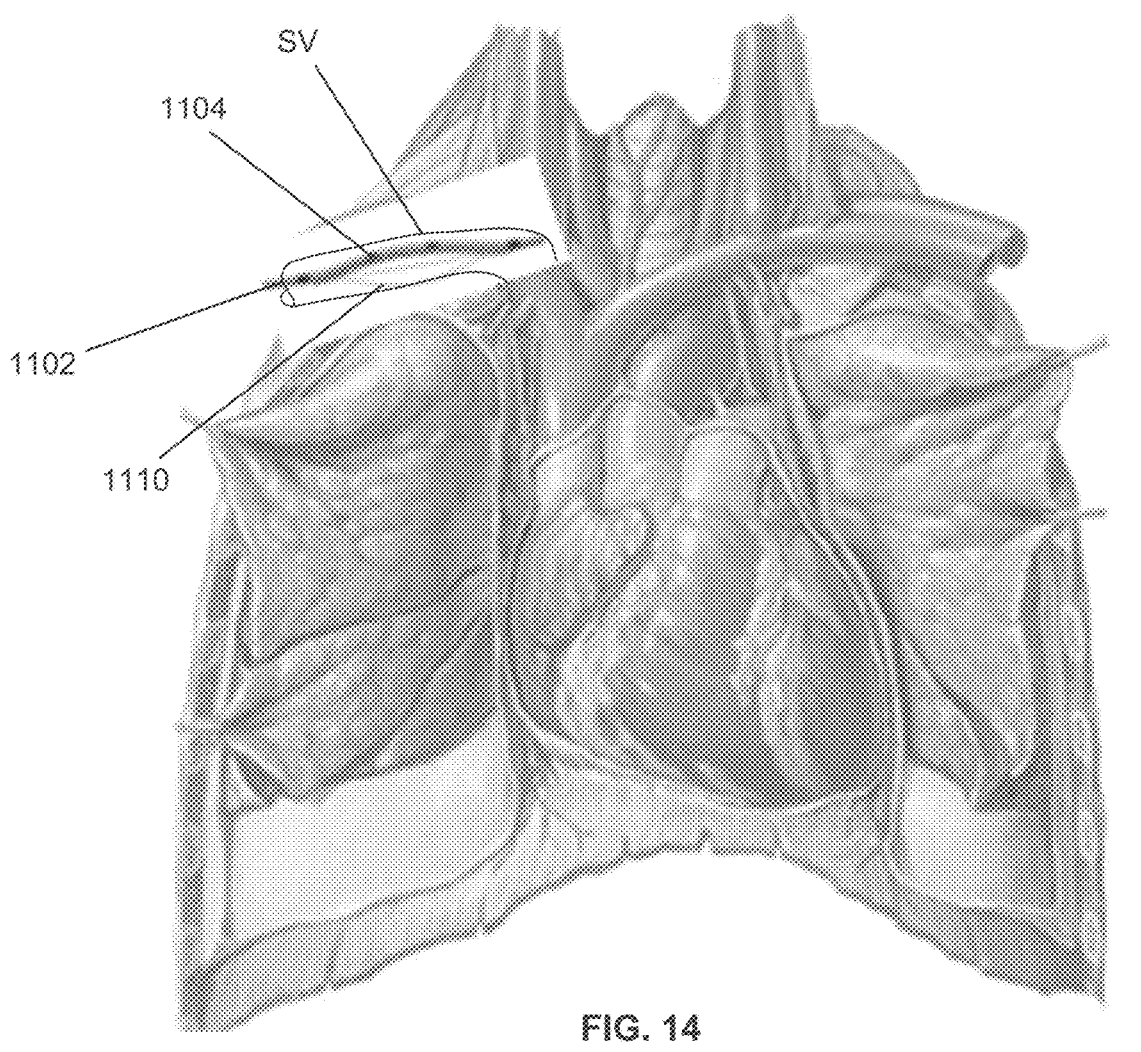
FIG. 14 shows a nitinol frame and lead system deployed inside the subclavian vein after removing the mapping sheath.

FIG. 14 shows an example where the frame 1110 and endovascular lead apparatus 1100 may be deployed inside the subclavian vein SV after removing the mapping sheath 1102. Alternatively, the lead system can be loaded onto a wire instead of a frame or tray 1300. The wire can be made of nitinol or another suitable material (e.g., PEEK, etc.).

Figure 15:
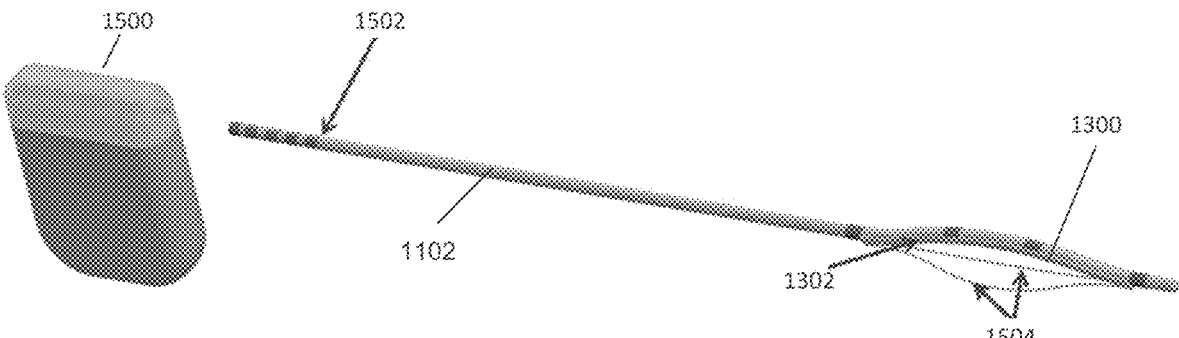
FIG. 15 shows the deployed nitinol frame lead system and implantable pulse generator (IPG).

FIG. 15 illustrates the endovascular lead apparatus 1100 attached or attachable to an implantable pulse generator (IPG) 1500 which may be implanted within the patient body or which may be located external to the patient body. The IPG 1500 may be electrically coupled to the mapping sheath 1102 through one or more electrical connectors or contact leads so that the IPG 1500 is electrically coupled to the electrodes located at the distal end of the device. As shown, the IPG 1500 can be electrically coupled to the proximal portion 1106 of the sheath 1102 at one or more contact leads 1502 positioned at a proximal end of the sheath 1102 and can deliver energy from the proximal portion 1106 of the apparatus 1100 to the distal portion 1108 of the sheath 1100. In some variations, the IPG 1500 can comprise a transducer for delivering electrical energy to the electrodes using an energy source such as ultrasound. The electrical energy generated can have a frequency between, e.g., 1 Hz and 400 Hz. For example, a frequency of an electrical impulse can be set at a relatively low frequency (between about 1 Hz to 10 Hz), a medium frequency (between about 10 Hz to 150 Hz), and a high frequency (between about 150 Hz to 400 Hz). In another variation, the lead system can be loaded onto one or more wires 1504 instead of a frame or tray 1300. The one or more wires 1504 can be made of nitinol or another suitable material (e.g., PEEK, etc.).

Alternatively, the wires within a lumen of the catheter 1102 can include the one or more wires 1504 used to urge the electrodes against the interior of the vessel wall. The neurostimulation lead apparatus thus can be constructed with a hollow lumen or channel 1302 defined through the sheath 1102 where the nitinol wire 1504 can be inserted. Upon removal of the mapping sheath 1102, the nitinol wires 1504 may be expanded (either self-expanding or expanded via actuation) to the intended diameter allowing the neurostimulation lead to be placed against the vessel wall in proximity to the nerve to be treated.

Figure 16:
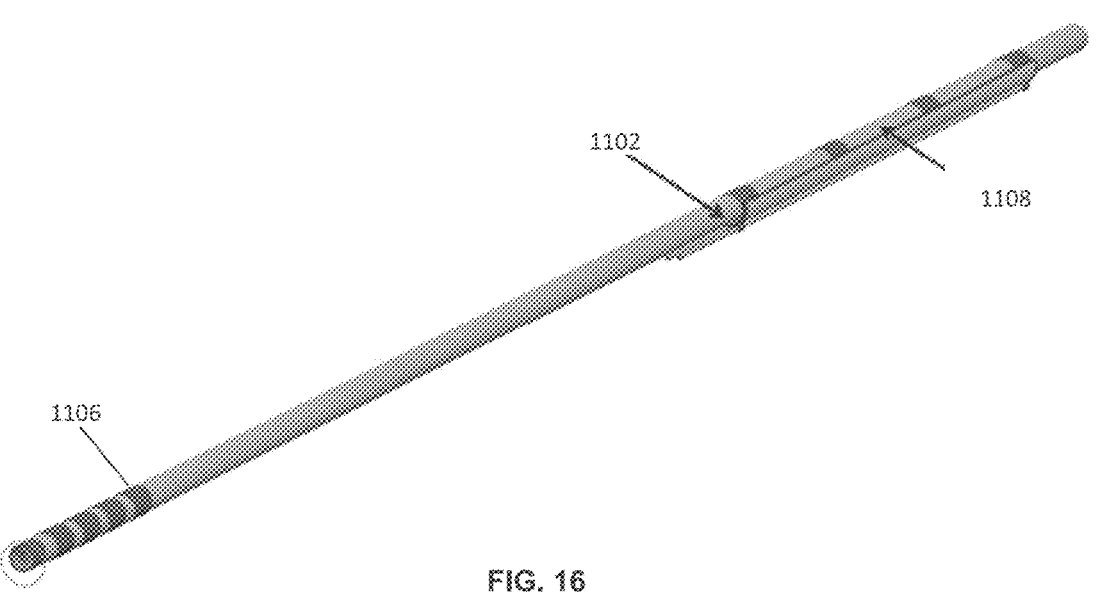
FIG. 16 shows the collapsed nitinol frame with neurostimulation lead system.

FIG. 16 shows a perspective view of the neurostimulation lead apparatus 1100 and the nitinol frame 1110 in its collapsed configuration. In one variation, the outer diameter of the sheath 1102 can be, e.g., about 7 Fr. The lead can include one or more electrodes 1104, e.g., 2-8 electrodes, where the electrodes may be spaced apart from, e.g., about 2 mm to about 5 mm. The electrodes 1104 can be equally separated from each other. Alternatively, the electrode separation can be arbitrary, uniform, or non-uniform. For example, the distal electrodes 1104 can be, e.g., 5 mm from one another, while proximal electrodes 1104 can be, e.g., 2 mm, from one another. There can be multiple configurations of electrode separation in one lead.

The electrodes 1104 can be made of various conductive materials, e.g., gold, iridium, palladium, a gold-palladium-rhodium alloy, rhodium, etc., or a combination thereof. In some embodiments, the electrodes 1104 can be made of a metallic composite with a high charge injection capacity (e.g., a platinum-iridium alloy or composite).

Figure 17:
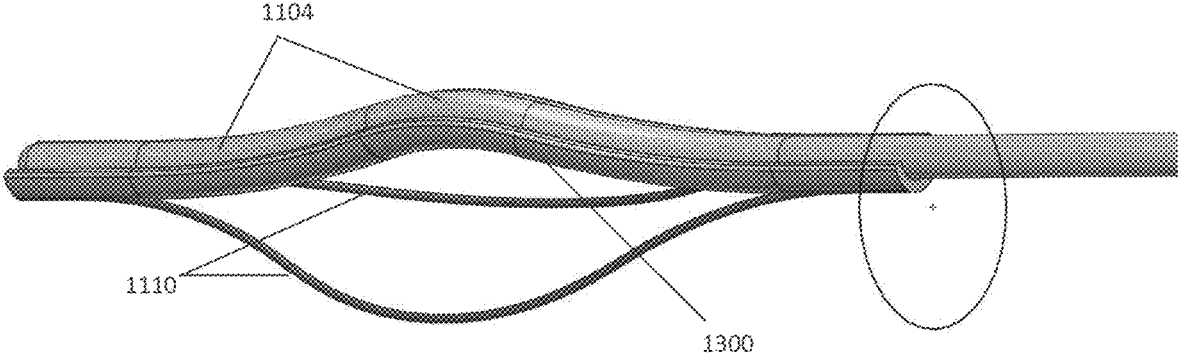
FIG. 17 shows an expanded version of the distal end of the neurostimulation lead system including the nitinol frame and the lead.

FIG. 17 shows a perspective detail view of another variation of the distal end of the neurostimulation lead including the nitinol frame 1110 and electrodes 1104. The tray 1300 and frame 1110 can be attached along a side of the frame 1110 when the frame 1110 is in the deployed configuration. The nitinol frame 1110 can be reconfigured into a non-linear shape and can abut the inner walls of the vessel to urge the tray 1300 and electrodes 1104 into contact with the opposite portion of the inner wall into proximity to the phrenic nerve for treatment.

The device can be used in another locations within a body, including but not limited to: the carotid artery, the vagus nerve, the cervical sympathetic ganglion, the aorta, the vagus nerve, the superior mesenteric ganglion, the inferior mesenteric ganglion, the renal artery, the renal nerves, the subclavian artery, the brachial plexus, the common hepatic artery, the gastroduodenal artery, the iliac artery, and the splanchnic nerves.

Figure 18:
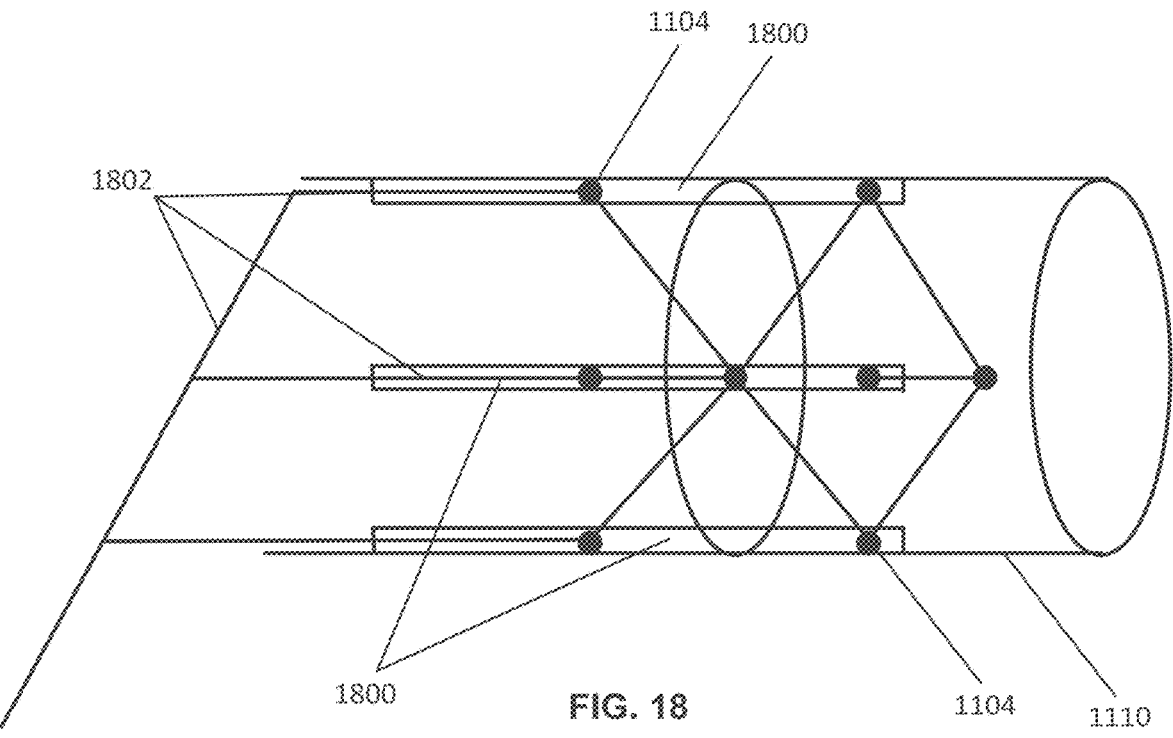
FIG. 18 shows a symmetrical nitinol frame with prongs loaded with leads.

FIG. 18 shows a symmetrical nitinol frame 1110 having multiple prongs 1800 (e.g., anywhere from two, three, four, five, etc.) which may deploy into an extended scaffold-like structure with each of the prongs 1800 having one or more stimulation electrodes 1104. This configuration allows for multiple electrodes configurations to identify most optimum electrodes (e.g., pairs or higher numbers) and optimum threshold settings between at least two of the prongs 1800. For instance, two or three prongs 1800 may be used to apply the stimulation in a cross-cross configuration.

The prongs 1800 can be coupled to the frame 1110 and can comprise wires 1802 or leads extending thereon which can couple to electrodes 1104 placed at different areas on the frame 1110. The frame 1110 can be shaped to expand and collapse with the electrodes 1104 and wires 1802 maintaining their positions relative to each other. The variation in FIG. 18 shows a cross-cross stimulation selection, though it should be understood that other shapes and configurations can be designed (e.g., circular, elliptical, etc.). Electrodes 1104 can be placed on frame 1110 through any number of attachment mechanisms such as by welding or crimping a conductive insulated wire assembly directly onto the frame 1110 and/or each individual electrode.

The frame can contain stress and strain in strategic locations of the scaffold where diametric contraction or expansion is translated as relative angular displacement of struts. Diametric contraction or expansion, for example, can occur when the frame is crimped, expanded at deployment, or over-expanded at deployment. The frame can contain the stress and strain in the peaks and valleys of the frame and the angular arrangement of the struts is designed to allow a finite amount of over-expansion beyond the original intended diameter. Any expansion beyond the predetermined level may cause strut elongation, reduced radial force, increased diametric recoil, and decreased structural integrity and fatigue life. Solution casting a frame having such design characteristics provides another way of optimizing the frame.

Wires 1802 can be made in part of any number of conductive materials, e.g., platinum tungsten, gold, aluminum, nitinol wire, rhodium, iridium, nickel, nickel-chromium alloy, gold-palladium-rhodium alloy, chromium-nickel-molybdenum alloy, and/or stainless steel, etc. In addition to nitinol, the frame 1110 can be made at least in part of, e.g., stainless steel, gold, platinum, nickel, titanium, tungsten, aluminum, nickel-chromium alloy, gold-palladium-rhodium alloy, chromium-nickel-molybdenum alloy, iridium, rhodium, or a combination thereof. The frame can also be made in part of a shape memory polymer.

Figure 19:
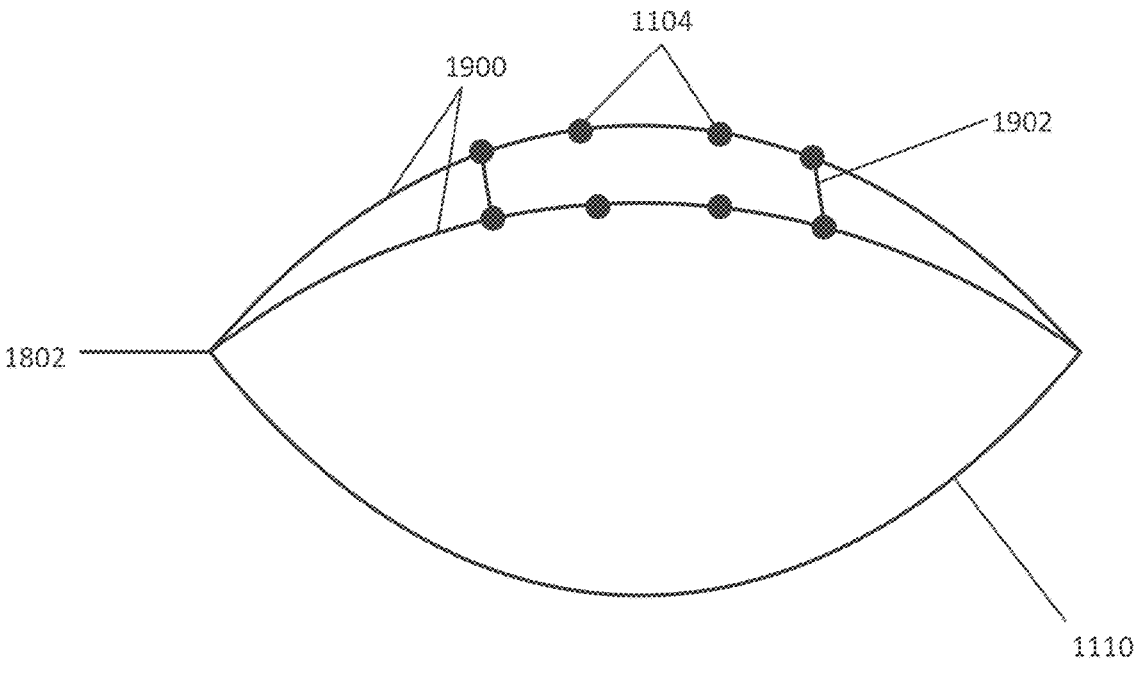
FIG. 19 shows an asymmetrical nitinol frame with neurostimulation leads or electrodes.

FIG. 19 shows yet another variation of an asymmetrical nitinol frame having neurostimulation leads and electrodes 1104 concentrated along a select portion of the frame so that the electrodes 1104 along the frame may be directed towards or near the nerve to be stimulated. One example may utilize four poles where the nitinol wires 1900 are asymmetric from one another and can have, e.g., about 2 mm to about 3 mm, distance between the wires 1900. One or more stent links 1902 which may extend between adjacent longitudinal scaffold members can be utilized between the wires to provide for stability during expansion or deployment.

While the nitinol frame 1110 may be released from a constrained, delivery configuration to an unconstrained, expanded configuration when released, a number of various methods and devices may be implemented to control the expansion of the nitinol frame to appose to the vessel wall in a manner similar to stent expansion and the frames may also be locked into place to minimize expansion.

In any of the variations described where multiple members of the nitinol frame 1110 are implemented, each of the individual members may be coupled with one another at a common connection point such as the distal and/or proximal ends of the frame. However, in other variations, each of the individual members may be arranged independently from one another rather than having a common connection point. In yet other variations, the individual members may be connected to one another at a proximal or distal end while the opposing end remains independent of one another.

Yet another variation may utilize one or more of the members of the frame being connected to the elongate device at a single end. In one example, the proximal ends of the frame members, e.g., three members, may be attached at their proximal ends to the elongate device such that the members upon expansion may open or flare into a configuration where the distal ends of the members extend away from elongate device.

In yet another variation, the leads may be integrated directly into the nitinol frame rather than having the leads separately located along the distal portion of the elongate device. In this manner, the frame may reconfigure into its expanded configuration into contact against the tissue walls where the leads may directly contact the tissue as well via the frame. Treatment may be implemented by electrical stimulation being delivered through the frame members instead.

Figure 20A:
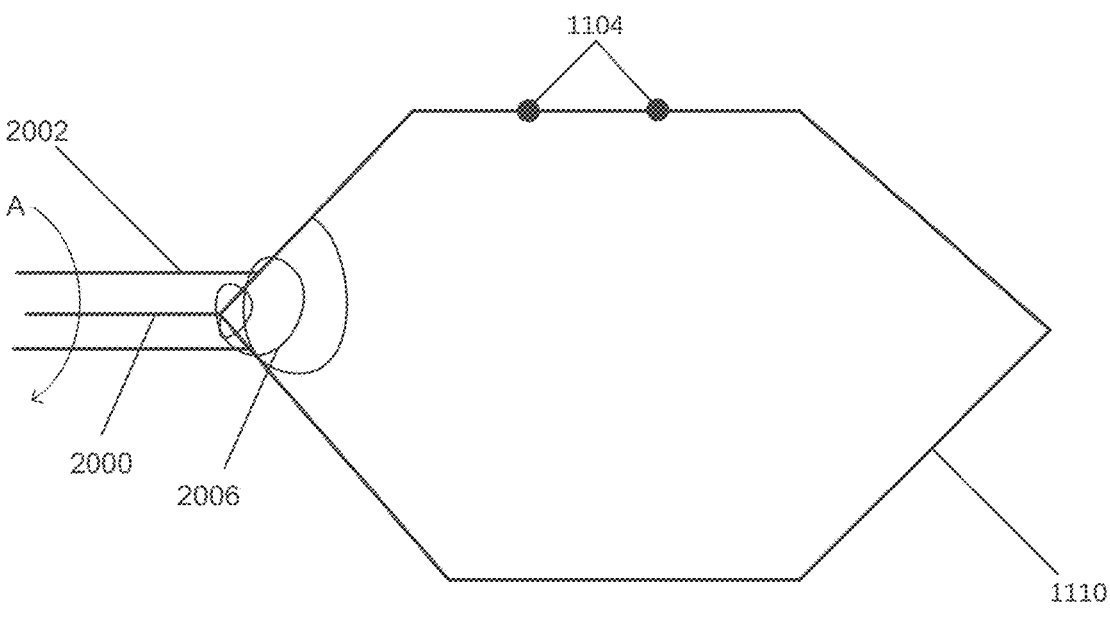
FIGS. 20A and 20B show methods for locking nitinol frame from migration and further expansion.

Given that vessel walls are compliant, the frame 1110 can be constrained to prevent any inadvertent nitinol expansion over time that may cause vessel wall injury or perforation. In one variation, FIG. 20A illustrates a side view of a rotatable tether mechanism 2006 attached to an end, such as the proximal end, of the nitinol frame 1110. A flexible shaft 2002 can be positioned through the length of the elongate sheath and the flexible shaft may be rotatable about its longitudinal axis, as seen by the arrow A in FIG. 20A. A distal end of the shaft may incorporate the rotatable tether mechanism 2006 such as a helical member which encompasses the proximal ends of the reconfigurable frame 1110. Rotation of the helical member in a first direction may expand the frame into its expanded configuration and rotation in a second opposite direction may collapse the frame back to its low-profile configuration. The controlled expansion of the nitinol/PEEK or other type material frame may be deployed into contact against the vessel wall (e.g., with the aid of imaging) in a controlled expansion.

Once the desired expansion is reached, the shaft 2002 of the tethering mechanism can be locked to thereby prevent or minimize the nitinol frame 1110 from further expansion. The expansion of the nitinol frame 1110 through the locking mechanism can be adjusted in such a way that the user can determine how many millimeters the nitinol frame 1110 has expanded. Markers and the number of rotations can guide the user to expand the frame to a desired diameter. This locking mechanism attached to the neurostimulation lead may also prevent the frame migration when the lead is attached to the IPG 1500.

Figure 20B:
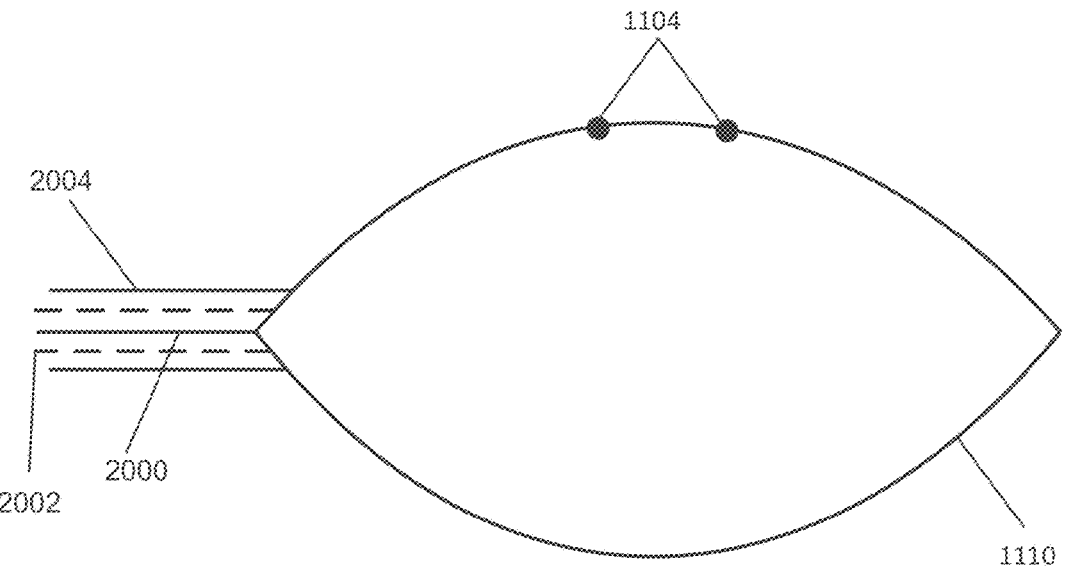

FIG. 20B shows a side view of yet another variation for controlling the expansion or collapse of the nitinol frame 1110. A push-pull sleeve 2004 or shaft can be slidably positioned over the length of the elongate shaft 2002 (shown in dashed lines for clarity) such that the distal end of the push-pull sleeve 2004 is slidably connected to a proximal portion or end of the nitinol frame. Once the frame 1110 is ready for expansion, the push-pull sleeve 2004 can be pulled proximally to allow for the expansion of the frame to appose against the vessel. A position of the push-pull sleeve 2004 may be locked relative to the lead body outside of the vessel to prevent the further expansion of the frame 1110. The body can be twisted, terminated, and removed from the lead body while the frame 1110 is locked in the position. Alternatively, the push-pull sleeve 2004 can be part of the lead body and in case of lead repositioning or removal, it can un-lock the frame 1110 and collapse it by winding it down for removal from the vessel.

An alternative mechanism incorporates a flexible tether 2000 coupled to a distal portion or end of the frame 1110. As pulling of the tether 2000 may tension it due to the reconfiguration of the frame from its deployed configuration to its expanded configuration, maintaining tension upon the tether 2000 may maintain the expanded configuration of the frame. A securement mechanism, such as a friction lock, on a proximal portion of the tensioning tether may lock the tether 2000 in place. The securement mechanism may be configured to automatically release, e.g., by a retrieval catheter or a cutting mechanism which may cut the tether 2000.

The applications of the devices and methods discussed above are not limited to treatments for disordered breathing but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

As a person skilled in the art will recognize from the previous detailed description and figures that modifications and changes may be made to the preferred embodiments of the invention without departing from the scope of this invention defined in the following claims.

We claim:

1. A method of stimulating a nerve, comprising:

advancing an elongate body within a vessel and into proximity of a nerve body to be stimulated;

confirming a location of the nerve body via one or more mapping electrodes positioned along a mapping sleeve which is configured to isolate the one or more mapping electrodes from the elongate body; and exposing a distal end of the elongate body by retracting the mapping sleeve relative to the elongate body once the location of the nerve body is confirmed such that an inner sleeve having one or more frame members is exposed along the distal end;

reconfiguring the one or more frame members to urge one or more treatment electrodes along the inner sleeve into contact against an inner surface of the vessel;

actuating the one or more treatment electrodes positioned against the inner surface to deliver a treatment stimulation through the inner surface and into the nerve body.

2. The method of claim 1 wherein advancing the elongate body comprises advancing the elongate body within a subclavian vein.

3. The method of claim 2 wherein advancing the elongate body within the subclavian vein comprises advancing into proximity of a phrenic nerve to be stimulated.

4. The method of claim 1 wherein confirming the location of the nerve body comprises delivering electrical stimulation through the one or more mapping electrodes and monitoring an effect on the phrenic nerve.

5. The method of claim 1 wherein exposing the distal end of the elongate body comprises sliding a sheath proximally relative to the elongate body to expose the distal end.

6. The method of claim 5 wherein reconfiguring the one or more frame members comprises reconfiguring the one or more frame members in a controlled manner via a locking mechanism.

7. The method of claim 5 further comprising reconfiguring the one or more frame members in a controlled manner via a push-pull sleeve.

8. The method of claim 5 further comprising reconfiguring the one or more frame members in a controlled manner via a flexible tether.

9. The method of claim 1 wherein actuating the one or more treatment electrodes comprises actuating via a pulse generator in electrical communication with the elongate body.

* * * * *